(12) United States Patent
Epshtein

(10) Patent No.: US 8,617,555 B2
(45) Date of Patent: Dec. 31, 2013

(54) PHARMACEUTICAL COMPOSITIONS COMPRISING ACTIVATED-POTENTIATED ANTIBODIES TO HUMAN INSULIN RECEPTOR AND ENDOTHELIAL NITRIC OXIDE (NO) SYNTHASE

(75) Inventor: Oleg Iliich Epshtein, Moscow (RU)

(73) Assignee: Oleg I. Epshtein (RU)

( * ) Notice: Subject to any disclaimer, the term of this patent is extended or adjusted under 35 U.S.C. 154(b) by 0 days.

(21) Appl. No.: 13/135,891

(22) Filed: Jul. 15, 2011

(65) Prior Publication Data
US 2013/0064824 A1 Mar. 14, 2013

(30) Foreign Application Priority Data

Jul. 21, 2010 (RU) ................................ 2010130348
Jul. 1, 2011 (RU) ................................ 2011127051

(51) Int. Cl.
*A61K 39/395* (2006.01)
*C07K 16/00* (2006.01)
*C12P 21/08* (2006.01)

(52) U.S. Cl.
USPC ................. 424/158.1; 424/139.1; 424/143.1; 424/146.1; 530/387.1; 530/387.9; 530/388.22; 530/388.24; 530/388.26

(58) Field of Classification Search
None
See application file for complete search history.

(56) References Cited

U.S. PATENT DOCUMENTS

| 6,933,272 | B1 * | 8/2005 | Helmerhorst et al. | ........... 514/75 |
| 7,396,659 | B2 * | 7/2008 | Singh | ............................. 435/25 |
| 7,700,096 | B2 * | 4/2010 | Epshtein et al. | ........... 424/130.1 |
| 2011/0230401 | A1 * | 9/2011 | Artymiuk et al. | .............. 514/5.9 |

FOREIGN PATENT DOCUMENTS

| EP | 1547612 A1 | 6/2005 |
| EP | 2036574 A1 | 3/2009 |

OTHER PUBLICATIONS

E. Ernst: "A systematic review of systematic reviews of homeopathy", British Journal of Clinical Pharmacology, vol. 54, No. 6, Dec. 1, 2002, pp. 577-582.
Shang A et al: "Are the clinical effects of homoeopathy placebo effects? Comparative study of placebo-controlled trials of homoeopathy and allopathy", The Lancet, Lancet Limited. London, GB, vol. 366, No. 9487, Aug. 27, 2005, pp. 726-732.
Notification of Transmittal of International Search Report and Written Opinion dated Feb. 8, 2012 for corresponding International Patent Application No. PCT/IB2011/002177.
International Search Report dated Aug. 2, 2012 for corresponding International Patent Application No. PCT/IB2011/002177.
Written Opinion of the International Searching Authority for corresponding International Patent Application No. PCT/IB2011/002177.

* cited by examiner

*Primary Examiner* — Robert Landsman
(74) *Attorney, Agent, or Firm* — Pergament Gilman & Cepeda LLP

(57) ABSTRACT

The present application provides a pharmaceutical composition for administration to a patient suffering from diabetes and other metabolic disorders, the composition comprises a) an activated-potentiated form of an antibody to human insulin receptor, and b) an activated-potentiated form of an antibody to endothelial NO-synthase.

12 Claims, 6 Drawing Sheets

SEQUENCE LISTING

<160> NUMBER OF SEQ ID NOS: 22

<210> SEQ ID NO 1
<211> LENGTH: 735
<212> TYPE: PRT
<213> ORGANISM: Homo sapiens
<220> FEATURE:
<221> NAME/KEY: SOURCE
<222> LOCATION: 1..735
<223> OTHER INFORMATION: /mol_type="protein"
    /organism="Homo sapiens"

-continued

```
<400> SEQUENCE: 1

His Leu Tyr Pro Gly Glu Val Cys Pro Gly Met Asp Ile Arg Asn Asn
1               5                   10                  15

Leu Thr Arg Leu His Glu Leu Glu Asn Cys Ser Val Ile Glu Gly His
            20                  25                  30

Leu Gln Ile Leu Leu Met Phe Lys Thr Arg Pro Glu Asp Phe Arg Asp
        35                  40                  45

Leu Ser Phe Pro Lys Leu Ile Met Ile Thr Asp Tyr Leu Leu Leu Phe
    50                  55                  60

Arg Val Tyr Gly Leu Glu Ser Leu Lys Asp Leu Phe Pro Asn Leu Thr
65                  70                  75                  80

Val Ile Arg Gly Ser Arg Leu Phe Phe Asn Tyr Ala Leu Val Ile Phe
                85                  90                  95

Glu Met Val His Leu Lys Glu Leu Gly Leu Tyr Asn Leu Met Asn Ile
            100                 105                 110

Thr Arg Gly Ser Val Arg Ile Glu Lys Asn Asn Glu Leu Cys Tyr Leu
        115                 120                 125

Ala Thr Ile Asp Trp Ser Arg Ile Leu Asp Ser Val Glu Asp Asn Tyr
    130                 135                 140

Ile Val Leu Asn Lys Asp Asp Asn Glu Glu Cys Gly Asp Ile Cys Pro
145                 150                 155                 160

Gly Thr Ala Lys Gly Lys Thr Asn Cys Pro Ala Thr Val Ile Asn Gly
                165                 170                 175

Gln Phe Val Glu Arg Cys Trp Thr His Ser His Cys Gln Lys Val Cys
            180                 185                 190

Pro Thr Ile Cys Lys Ser His Gly Cys Thr Ala Glu Gly Leu Cys Cys
        195                 200                 205

His Ser Glu Cys Leu Gly Asn Cys Ser Gln Pro Asp Asp Pro Thr Lys
    210                 215                 220

Cys Val Ala Cys Arg Asn Phe Tyr Leu Asp Gly Arg Cys Val Glu Thr
225                 230                 235                 240

Cys Pro Pro Pro Tyr Tyr His Phe Gln Asp Trp Arg Cys Val Asn Phe
                245                 250                 255

Ser Phe Cys Gln Asp Leu His His Lys Cys Lys Asn Ser Arg Arg Gln
            260                 265                 270

Gly Cys His Gln Tyr Val Ile His Asn Asn Lys Cys Ile Pro Glu Cys
        275                 280                 285

Pro Ser Gly Tyr Thr Met Asn Ser Ser Asn Leu Leu Cys Thr Pro Cys
    290                 295                 300

Leu Gly Pro Cys Pro Lys Val Cys His Leu Leu Glu Gly Glu Lys Thr
305                 310                 315                 320

Ile Asp Ser Val Thr Ser Ala Gln Glu Leu Arg Gly Cys Thr Val Ile
                325                 330                 335

Asn Gly Ser Leu Ile Ile Asn Ile Arg Gly Gly Asn Asn Leu Ala Ala
            340                 345                 350

Glu Leu Glu Ala Asn Leu Gly Leu Ile Glu Glu Ile Ser Gly Tyr Leu
        355                 360                 365

Lys Ile Arg Arg Ser Tyr Ala Leu Val Ser Leu Ser Phe Phe Arg Lys
    370                 375                 380

Leu Arg Leu Ile Arg Gly Glu Thr Leu Glu Ile Gly Asn Tyr Ser Phe
385                 390                 395                 400

Tyr Ala Leu Asp Asn Gln Asn Leu Arg Gln Leu Trp Asp Trp Ser Lys
                405                 410                 415
```

His Asn Leu Thr Ile Thr Gln Gly Lys Leu Phe Phe His Tyr Asn Pro
            420                 425                 430

Lys Leu Cys Leu Ser Glu Ile His Lys Met Glu Val Ser Gly Thr
            435                 440                 445

Lys Gly Arg Gln Glu Arg Asn Asp Ile Ala Leu Lys Thr Asn Gly Asp
450                 455                 460

Gln Ala Ser Cys Glu Asn Glu Leu Leu Lys Phe Ser Tyr Ile Arg Thr
465                 470                 475                 480

Ser Phe Asp Lys Ile Leu Leu Arg Trp Glu Pro Tyr Trp Pro Pro Asp
                485                 490                 495

Phe Arg Asp Leu Leu Gly Phe Met Leu Phe Tyr Lys Glu Ala Pro Tyr
            500                 505                 510

Gln Asn Val Thr Glu Phe Asp Gly Gln Asp Ala Cys Gly Ser Asn Ser
            515                 520                 525

Trp Thr Val Val Asp Ile Asp Pro Pro Leu Arg Ser Asn Asp Pro Lys
530                 535                 540

Ser Gln Asn His Pro Gly Trp Leu Met Arg Gly Leu Lys Pro Trp Thr
545                 550                 555                 560

Gln Tyr Ala Ile Phe Val Lys Thr Leu Val Thr Phe Ser Asp Glu Arg
                565                 570                 575

Arg Thr Tyr Gly Ala Lys Ser Asp Ile Ile Tyr Val Gln Thr Asp Ala
            580                 585                 590

Thr Asn Pro Ser Val Pro Leu Asp Pro Ile Ser Val Ser Asn Ser Ser
            595                 600                 605

Ser Gln Ile Ile Leu Lys Trp Lys Pro Pro Ser Asp Pro Asn Gly Asn
610                 615                 620

Ile Thr His Tyr Leu Val Phe Trp Glu Arg Gln Ala Glu Asp Ser Glu
625                 630                 635                 640

Leu Phe Glu Leu Asp Tyr Cys Leu Lys Gly Leu Lys Leu Pro Ser Arg
                645                 650                 655

Thr Trp Ser Pro Pro Phe Glu Ser Glu Asp Ser Gln Lys His Asn Gln
            660                 665                 670

Ser Glu Tyr Glu Asp Ser Ala Gly Glu Cys Cys Ser Cys Pro Lys Thr
            675                 680                 685

Asp Ser Gln Ile Leu Lys Glu Leu Glu Ser Ser Phe Arg Lys Thr
690                 695                 700

Phe Glu Asp Tyr Leu His Asn Val Val Phe Val Pro Arg Lys Thr Ser
705                 710                 715                 720

Ser Gly Thr Gly Ala Glu Asp Pro Arg Pro Ser Arg Lys Arg Arg
                725                 730                 735

<210> SEQ ID NO 2
<211> LENGTH: 14
<212> TYPE: PRT
<213> ORGANISM: Homo sapiens
<220> FEATURE:
<221> NAME/KEY: SOURCE
<222> LOCATION: 1..14
<223> OTHER INFORMATION: /mol_type="protein"
      /organism="Homo sapiens"

<400> SEQUENCE: 2

Leu Gly Leu Tyr Asn Leu Met Asn Ile Thr Arg Gly Ser Val
1               5                   10

<210> SEQ ID NO 3
<211> LENGTH: 13
<212> TYPE: PRT

```
<213> ORGANISM: Homo sapiens
<220> FEATURE:
<221> NAME/KEY: SOURCE
<222> LOCATION: 1..13
<223> OTHER INFORMATION: /mol_type="protein"
      /organism="Homo sapiens"

<400> SEQUENCE: 3

Lys Gly Lys Thr Asn Cys Pro Ala Thr Val Ile Asn Gly
1               5                   10

<210> SEQ ID NO 4
<211> LENGTH: 13
<212> TYPE: PRT
<213> ORGANISM: Homo sapiens
<220> FEATURE:
<221> NAME/KEY: SOURCE
<222> LOCATION: 1..13
<223> OTHER INFORMATION: /mol_type="protein"
      /organism="Homo sapiens"

<400> SEQUENCE: 4

Trp Ser Lys His Asn Leu Thr Ile Thr Gln Gly Lys Leu
1               5                   10

<210> SEQ ID NO 5
<211> LENGTH: 20
<212> TYPE: PRT
<213> ORGANISM: Homo sapiens
<220> FEATURE:
<221> NAME/KEY: SOURCE
<222> LOCATION: 1..20
<223> OTHER INFORMATION: /mol_type="protein"
      /organism="Homo sapiens"

<400> SEQUENCE: 5

Asn Val Thr Glu Phe Asp Gly Gln Asp Ala Cys Gly Ser Asn Ser Trp
1               5                   10                  15

Thr Val Val Asp
            20

<210> SEQ ID NO 6
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 6

Asp Ile Ile Tyr Val Gln Thr Asp Ala Thr
1               5                   10

<210> SEQ ID NO 7
<211> LENGTH: 18
<212> TYPE: PRT
<213> ORGANISM: Homo sapiens
<220> FEATURE:
<221> NAME/KEY: SOURCE
<222> LOCATION: 1..18
<223> OTHER INFORMATION: /mol_type="protein"
      /organism="Homo sapiens"

<400> SEQUENCE: 7

Tyr Glu Asp Ser Ala Gly Glu Cys Cys Ser Cys Pro Lys Thr Asp Ser
1               5                   10                  15

Gln Ile
```

```
<210> SEQ ID NO 8
<211> LENGTH: 620
<212> TYPE: PRT
<213> ORGANISM: Homo sapiens
<220> FEATURE:
<221> NAME/KEY: SOURCE
<222> LOCATION: 1..620
<223> OTHER INFORMATION: /mol_type="protein"
      /organism="Homo sapiens"

<400> SEQUENCE: 8

Ser Leu Gly Asp Val Gly Asn Val Thr Val Ala Val Pro Thr Val Ala
1               5                   10                  15

Ala Phe Pro Asn Thr Ser Ser Thr Ser Val Pro Thr Ser Pro Glu Glu
                20                  25                  30

His Arg Pro Phe Glu Lys Val Val Asn Lys Glu Ser Leu Val Ile Ser
            35                  40                  45

Gly Leu Arg His Phe Thr Gly Tyr Arg Ile Glu Leu Gln Ala Cys Asn
    50                  55                  60

Gln Asp Thr Pro Glu Glu Arg Cys Ser Val Ala Ala Tyr Val Ser Ala
65                  70                  75                  80

Arg Thr Met Pro Glu Ala Lys Ala Asp Asp Ile Val Gly Pro Val Thr
                85                  90                  95

His Glu Ile Phe Glu Asn Asn Val Val His Leu Met Trp Gln Glu Pro
            100                 105                 110

Lys Glu Pro Asn Gly Leu Ile Val Leu Tyr Glu Val Ser Tyr Arg Arg
        115                 120                 125

Tyr Gly Asp Glu Glu Leu His Leu Cys Val Ser Arg Lys His Phe Ala
130                 135                 140

Leu Glu Arg Gly Cys Arg Leu Arg Gly Leu Ser Pro Gly Asn Tyr Ser
145                 150                 155                 160

Val Arg Ile Arg Ala Thr Ser Leu Ala Gly Asn Gly Ser Trp Thr Glu
                165                 170                 175

Pro Thr Tyr Phe Tyr Val Thr Asp Tyr Leu Asp Val Pro Ser Asn Ile
            180                 185                 190

Ala Lys Ile Ile Ile Gly Pro Leu Ile Phe Val Phe Leu Phe Ser Val
        195                 200                 205

Val Ile Gly Ser Ile Tyr Leu Phe Leu Arg Lys Arg Gln Pro Asp Gly
210                 215                 220

Pro Leu Gly Pro Leu Tyr Ala Ser Ser Asn Pro Glu Tyr Leu Ser Ala
225                 230                 235                 240

Ser Asp Val Phe Pro Cys Ser Val Tyr Val Pro Asp Glu Trp Glu Val
                245                 250                 255

Ser Arg Glu Lys Ile Thr Leu Leu Arg Glu Leu Gly Gln Gly Ser Phe
            260                 265                 270

Gly Met Val Tyr Glu Gly Asn Ala Arg Asp Ile Ile Lys Gly Glu Ala
        275                 280                 285

Glu Thr Arg Val Ala Val Lys Thr Val Asn Glu Ser Ala Ser Leu Arg
290                 295                 300

Glu Arg Ile Glu Phe Leu Asn Glu Ala Ser Val Met Lys Gly Phe Thr
305                 310                 315                 320

Cys His His Val Val Arg Leu Leu Gly Val Val Ser Lys Gly Gln Pro
                325                 330                 335

Thr Leu Val Val Met Glu Leu Met Ala His Gly Asp Leu Lys Ser Tyr
            340                 345                 350
```

-continued

```
Leu Arg Ser Leu Arg Pro Glu Ala Glu Asn Asn Pro Gly Arg Pro Pro
        355                 360                 365

Pro Thr Leu Gln Glu Met Ile Gln Met Ala Ala Glu Ile Ala Asp Gly
    370                 375                 380

Met Ala Tyr Leu Asn Ala Lys Lys Phe Val His Arg Asp Leu Ala Ala
385                 390                 395                 400

Arg Asn Cys Met Val Ala His Asp Phe Thr Val Lys Ile Gly Asp Phe
                405                 410                 415

Gly Met Thr Arg Asp Ile Tyr Glu Thr Asp Tyr Tyr Arg Lys Gly Gly
            420                 425                 430

Lys Gly Leu Leu Pro Val Arg Trp Met Ala Pro Glu Ser Leu Lys Asp
        435                 440                 445

Gly Val Phe Thr Thr Ser Ser Asp Met Trp Ser Phe Gly Val Val Leu
    450                 455                 460

Trp Glu Ile Thr Ser Leu Ala Glu Gln Pro Tyr Gln Gly Leu Ser Asn
465                 470                 475                 480

Glu Gln Val Leu Lys Phe Val Met Asp Gly Gly Tyr Leu Asp Gln Pro
                485                 490                 495

Asp Asn Cys Pro Glu Arg Val Thr Asp Leu Met Arg Met Cys Trp Gln
            500                 505                 510

Phe Asn Pro Lys Met Arg Pro Thr Phe Leu Glu Ile Val Asn Leu Leu
        515                 520                 525

Lys Asp Asp Leu His Pro Ser Phe Pro Glu Val Ser Phe Phe His Ser
    530                 535                 540

Glu Glu Asn Lys Ala Pro Glu Ser Glu Glu Leu Glu Met Glu Phe Glu
545                 550                 555                 560

Asp Met Glu Asn Val Pro Leu Asp Arg Ser Ser His Cys Gln Arg Glu
                565                 570                 575

Glu Ala Gly Gly Arg Asp Gly Gly Ser Ser Leu Gly Phe Lys Arg Ser
            580                 585                 590

Tyr Glu Glu His Ile Pro Tyr Thr His Met Asn Gly Gly Lys Lys Asn
        595                 600                 605

Gly Arg Ile Leu Thr Leu Pro Arg Ser Asn Pro Ser
    610                 615                 620
```

<210> SEQ ID NO 9
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
     /organism="Homo sapiens"

<400> SEQUENCE: 9

```
Lys Lys Asn Gly Arg Ile Leu Thr Leu Pro
1               5                   10
```

<210> SEQ ID NO 10
<211> LENGTH: 11
<212> TYPE: PRT
<213> ORGANISM: Homo sapiens
<220> FEATURE:
<221> NAME/KEY: SOURCE
<222> LOCATION: 1..11
<223> OTHER INFORMATION: /mol_type="protein"
     /organism="Homo sapiens"

<400> SEQUENCE: 10

```
Arg Ile Leu Thr Leu Pro Arg Ser Asn Pro Ser
1               5                   10
```

<210> SEQ ID NO 11
<211> LENGTH: 7
<212> TYPE: PRT
<213> ORGANISM: Homo sapiens
<220> FEATURE:
<221> NAME/KEY: SOURCE
<222> LOCATION: 1..7
<223> OTHER INFORMATION: /mol_type="protein"
      /organism="Homo sapiens"

<400> SEQUENCE: 11

```
Lys Asn Gly Arg Ile Leu Thr
1               5
```

<210> SEQ ID NO 12
<211> LENGTH: 17
<212> TYPE: PRT
<213> ORGANISM: Homo sapiens
<220> FEATURE:
<221> NAME/KEY: SOURCE
<222> LOCATION: 1..17
<223> OTHER INFORMATION: /mol_type="protein"
      /organism="Homo sapiens"

<400> SEQUENCE: 12

```
Gly Gly Lys Lys Asn Gly Arg Ile Leu Thr Leu Pro Arg Ser Asn Pro
1               5                   10                  15

Ser
```

<210> SEQ ID NO 13
<211> LENGTH: 18
<212> TYPE: PRT
<213> ORGANISM: Homo sapiens
<220> FEATURE:
<221> NAME/KEY: SOURCE
<222> LOCATION: 1..18
<223> OTHER INFORMATION: /mol_type="protein"
      /organism="Homo sapiens"

<400> SEQUENCE: 13

```
Asn Gly Gly Lys Lys Asn Gly Arg Ile Leu Thr Leu Pro Arg Ser Asn
1               5                   10                  15

Pro Ser
```

<210> SEQ ID NO 14
<211> LENGTH: 1382
<212> TYPE: PRT
<213> ORGANISM: Homo sapiens
<220> FEATURE:
<221> NAME/KEY: SOURCE
<222> LOCATION: 1..1382
<223> OTHER INFORMATION: /mol_type="protein"
      /organism="Homo sapiens"

<400> SEQUENCE: 14

```
Met Ala Thr Gly Gly Arg Arg Gly Ala Ala Ala Pro Leu Leu Val
1               5                   10                  15

Ala Val Ala Ala Leu Leu Leu Gly Ala Ala Gly His Leu Tyr Pro Gly
                20                  25                  30

Glu Val Cys Pro Gly Met Asp Ile Arg Asn Asn Leu Thr Arg Leu His
                35                  40                  45

Glu Leu Glu Asn Cys Ser Val Ile Glu Gly His Leu Gln Ile Leu Leu
                50                  55                  60
```

-continued

```
Met Phe Lys Thr Arg Pro Glu Asp Phe Arg Asp Leu Ser Phe Pro Lys
 65                  70                  75                  80

Leu Ile Met Ile Thr Asp Tyr Leu Leu Phe Arg Val Tyr Gly Leu
                 85                  90                  95

Glu Ser Leu Lys Asp Leu Phe Pro Asn Leu Thr Val Ile Arg Gly Ser
                100                 105                 110

Arg Leu Phe Phe Asn Tyr Ala Leu Val Ile Phe Glu Met Val His Leu
            115                 120                 125

Lys Glu Leu Gly Leu Tyr Asn Leu Met Asn Ile Thr Arg Gly Ser Val
        130                 135                 140

Arg Ile Glu Lys Asn Asn Glu Leu Cys Tyr Leu Ala Thr Ile Asp Trp
145                 150                 155                 160

Ser Arg Ile Leu Asp Ser Val Glu Asp Asn Tyr Ile Val Leu Asn Lys
                165                 170                 175

Asp Asp Asn Glu Glu Cys Gly Asp Ile Cys Pro Gly Thr Ala Lys Gly
            180                 185                 190

Lys Thr Asn Cys Pro Ala Thr Val Ile Asn Gly Gln Phe Val Glu Arg
        195                 200                 205

Cys Trp Thr His Ser His Cys Gln Lys Val Cys Pro Thr Ile Cys Lys
210                 215                 220

Ser His Gly Cys Thr Ala Glu Gly Leu Cys Cys His Ser Glu Cys Leu
225                 230                 235                 240

Gly Asn Cys Ser Gln Pro Asp Asp Pro Thr Lys Cys Val Ala Cys Arg
                245                 250                 255

Asn Phe Tyr Leu Asp Gly Arg Cys Val Glu Thr Cys Pro Pro Pro Tyr
            260                 265                 270

Tyr His Phe Gln Asp Trp Arg Cys Val Asn Phe Ser Phe Cys Gln Asp
        275                 280                 285

Leu His His Lys Cys Lys Asn Ser Arg Arg Gln Gly Cys His Gln Tyr
            290                 295                 300

Val Ile His Asn Asn Lys Cys Ile Pro Glu Cys Pro Ser Gly Tyr Thr
305                 310                 315                 320

Met Asn Ser Ser Asn Leu Leu Cys Thr Pro Cys Leu Gly Pro Cys Pro
                325                 330                 335

Lys Val Cys His Leu Leu Glu Gly Lys Thr Ile Asp Ser Val Thr
            340                 345                 350

Ser Ala Gln Glu Leu Arg Gly Cys Thr Val Ile Asn Gly Ser Leu Ile
        355                 360                 365

Ile Asn Ile Arg Gly Gly Asn Asn Leu Ala Ala Glu Leu Glu Ala Asn
370                 375                 380

Leu Gly Leu Ile Glu Glu Ile Ser Gly Tyr Leu Lys Ile Arg Arg Ser
385                 390                 395                 400

Tyr Ala Leu Val Ser Leu Ser Phe Phe Arg Lys Leu Arg Leu Ile Arg
                405                 410                 415

Gly Glu Thr Leu Glu Ile Gly Asn Tyr Ser Phe Tyr Ala Leu Asp Asn
            420                 425                 430

Gln Asn Leu Arg Gln Leu Trp Asp Trp Ser Lys His Asn Leu Thr Ile
        435                 440                 445

Thr Gln Gly Lys Leu Phe Phe His Tyr Asn Pro Lys Leu Cys Leu Ser
    450                 455                 460

Glu Ile His Lys Met Glu Glu Val Ser Gly Thr Lys Gly Arg Gln Glu
465                 470                 475                 480

Arg Asn Asp Ile Ala Leu Lys Thr Asn Gly Asp Gln Ala Ser Cys Glu
                485                 490                 495
```

```
Asn Glu Leu Leu Lys Phe Ser Tyr Ile Arg Thr Ser Phe Asp Lys Ile
            500                 505                 510

Leu Leu Arg Trp Glu Pro Tyr Trp Pro Asp Phe Arg Asp Leu Leu
        515                 520                 525

Gly Phe Met Leu Phe Tyr Lys Glu Ala Pro Tyr Gln Asn Val Thr Glu
    530                 535                 540

Phe Asp Gly Gln Asp Ala Cys Gly Ser Asn Ser Trp Thr Val Val Asp
545                 550                 555                 560

Ile Asp Pro Pro Leu Arg Ser Asn Asp Pro Lys Ser Gln Asn His Pro
                565                 570                 575

Gly Trp Leu Met Arg Gly Leu Lys Pro Trp Thr Gln Tyr Ala Ile Phe
            580                 585                 590

Val Lys Thr Leu Val Thr Phe Ser Asp Glu Arg Arg Thr Tyr Gly Ala
            595                 600                 605

Lys Ser Asp Ile Ile Tyr Val Gln Thr Asp Ala Thr Asn Pro Ser Val
            610                 615                 620

Pro Leu Asp Pro Ile Ser Val Ser Asn Ser Ser Ser Gln Ile Ile Leu
625                 630                 635                 640

Lys Trp Lys Pro Pro Ser Asp Pro Asn Gly Asn Ile Thr His Tyr Leu
                645                 650                 655

Val Phe Trp Glu Arg Gln Ala Glu Asp Ser Glu Leu Phe Glu Leu Asp
            660                 665                 670

Tyr Cys Leu Lys Gly Leu Lys Leu Pro Ser Arg Thr Trp Ser Pro Pro
            675                 680                 685

Phe Glu Ser Glu Asp Ser Gln Lys His Asn Gln Ser Glu Tyr Glu Asp
            690                 695                 700

Ser Ala Gly Glu Cys Cys Ser Cys Pro Lys Thr Asp Ser Gln Ile Leu
705                 710                 715                 720

Lys Glu Leu Glu Glu Ser Ser Phe Arg Lys Thr Phe Glu Asp Tyr Leu
                725                 730                 735

His Asn Val Val Phe Val Pro Arg Lys Thr Ser Ser Gly Thr Gly Ala
            740                 745                 750

Glu Asp Pro Arg Pro Ser Arg Lys Arg Arg Ser Leu Gly Asp Val Gly
        755                 760                 765

Asn Val Thr Val Ala Val Pro Thr Val Ala Ala Phe Pro Asn Thr Ser
    770                 775                 780

Ser Thr Ser Val Pro Thr Ser Pro Glu Glu His Arg Pro Phe Glu Lys
785                 790                 795                 800

Val Val Asn Lys Glu Ser Leu Val Ile Ser Gly Leu Arg His Phe Thr
                805                 810                 815

Gly Tyr Arg Ile Glu Leu Gln Ala Cys Asn Gln Asp Thr Pro Glu Glu
            820                 825                 830

Arg Cys Ser Val Ala Ala Tyr Val Ser Ala Arg Thr Met Pro Glu Ala
        835                 840                 845

Lys Ala Asp Asp Ile Val Gly Pro Val Thr His Glu Ile Phe Glu Asn
    850                 855                 860

Asn Val Val His Leu Met Trp Gln Glu Pro Lys Glu Pro Asn Gly Leu
865                 870                 875                 880

Ile Val Leu Tyr Glu Val Ser Tyr Arg Arg Tyr Gly Asp Glu Glu Leu
                885                 890                 895

His Leu Cys Val Ser Arg Lys His Phe Ala Leu Glu Arg Gly Cys Arg
            900                 905                 910

Leu Arg Gly Leu Ser Pro Gly Asn Tyr Ser Val Arg Ile Arg Ala Thr
```

-continued

```
            915                 920                 925
Ser Leu Ala Gly Asn Gly Ser Trp Thr Glu Pro Thr Tyr Phe Tyr Val
930                 935                 940

Thr Asp Tyr Leu Asp Val Pro Ser Asn Ile Ala Lys Ile Ile Ile Gly
945                 950                 955                 960

Pro Leu Ile Phe Val Phe Leu Phe Ser Val Val Ile Gly Ser Ile Tyr
                965                 970                 975

Leu Phe Leu Arg Lys Arg Gln Pro Asp Gly Pro Leu Gly Pro Leu Tyr
                980                 985                 990

Ala Ser Ser Asn Pro Glu Tyr Leu Ser Ala Ser Asp Val Phe Pro Cys
                995                 1000                1005

Ser Val Tyr Val Pro Asp Glu Trp Glu Val Ser Arg Glu Lys Ile Thr
1010                1015                1020

Leu Leu Arg Glu Leu Gly Gln Gly Ser Phe Gly Met Val Tyr Glu Gly
1025                1030                1035                1040

Asn Ala Arg Asp Ile Ile Lys Gly Glu Ala Glu Thr Arg Val Ala Val
                1045                1050                1055

Lys Thr Val Asn Glu Ser Ala Ser Leu Arg Glu Arg Ile Glu Phe Leu
                1060                1065                1070

Asn Glu Ala Ser Val Met Lys Gly Phe Thr Cys His His Val Val Arg
                1075                1080                1085

Leu Leu Gly Val Val Ser Lys Gly Gln Pro Thr Leu Val Val Met Glu
1090                1095                1100

Leu Met Ala His Gly Asp Leu Lys Ser Tyr Leu Arg Ser Leu Arg Pro
1105                1110                1115                1120

Glu Ala Glu Asn Asn Pro Gly Arg Pro Pro Thr Leu Gln Glu Met
                1125                1130                1135

Ile Gln Met Ala Ala Glu Ile Ala Asp Gly Met Ala Tyr Leu Asn Ala
                1140                1145                1150

Lys Lys Phe Val His Arg Asp Leu Ala Ala Arg Asn Cys Met Val Ala
                1155                1160                1165

His Asp Phe Thr Val Lys Ile Gly Asp Phe Gly Met Thr Arg Asp Ile
1170                1175                1180

Tyr Glu Thr Asp Tyr Tyr Arg Lys Gly Gly Lys Gly Leu Leu Pro Val
1185                1190                1195                1200

Arg Trp Met Ala Pro Glu Ser Leu Lys Asp Gly Val Phe Thr Thr Ser
                1205                1210                1215

Ser Asp Met Trp Ser Phe Gly Val Val Leu Trp Glu Ile Thr Ser Leu
                1220                1225                1230

Ala Glu Gln Pro Tyr Gln Gly Leu Ser Asn Glu Gln Val Leu Lys Phe
                1235                1240                1245

Val Met Asp Gly Gly Tyr Leu Asp Gln Pro Asp Asn Cys Pro Glu Arg
                1250                1255                1260

Val Thr Asp Leu Met Arg Met Cys Trp Gln Phe Asn Pro Lys Met Arg
1265                1270                1275                1280

Pro Thr Phe Leu Glu Ile Val Asn Leu Leu Lys Asp Asp Leu His Pro
                1285                1290                1295

Ser Phe Pro Glu Val Ser Phe Phe His Ser Glu Glu Asn Lys Ala Pro
                1300                1305                1310

Glu Ser Glu Glu Leu Glu Met Glu Phe Glu Asp Met Glu Asn Val Pro
                1315                1320                1325

Leu Asp Arg Ser Ser His Cys Gln Arg Glu Glu Ala Gly Gly Arg Asp
                1330                1335                1340
```

-continued

```
Gly Gly Ser Ser Leu Gly  Phe Lys Arg Ser Tyr Glu His Ile Pro
1345              1350                 1355                1360

Tyr Thr His Met Asn Gly Gly Lys Lys Asn  Gly Arg Ile Leu Thr Leu
                1365                 1370                1375

Pro Arg Ser Asn  Pro Ser
         1380

<210> SEQ ID NO 15
<211> LENGTH: 1205
<212> TYPE: PRT
<213> ORGANISM: Bos taurus
<220> FEATURE:
<221> NAME/KEY: SOURCE
<222> LOCATION: 1..1205
<223> OTHER INFORMATION: /mol_type="protein"
      /organism="Bos taurus"

<400> SEQUENCE: 15

Met Gly Asn Leu Lys Ser Val Gly Gln Glu Pro Gly Pro Cys Gly
1               5                   10                  15

Leu Gly Leu Gly Leu Gly Leu Gly Leu Cys Gly Lys Gln Gly Pro Ala
                20                  25                  30

Ser Pro Ala Pro Glu Pro Ser Arg Ala Pro Ala Pro Thr Pro His
        35                  40                  45

Ala Pro Asp His Ser Pro Ala Pro Asn Ser Pro Thr Leu Thr Arg Pro
        50                  55                  60

Pro Glu Gly Pro Lys Phe Pro Arg Val Lys Asn Trp Glu Leu Gly Ser
65                  70                  75                  80

Ile Thr Tyr Asp Thr Leu Cys Ala Gln Ser Gln Gln Asp Gly Pro Cys
                85                  90                  95

Thr Pro Arg Cys Cys Leu Gly Ser Leu Val Leu Pro Arg Lys Leu Gln
                100                 105                 110

Thr Arg Pro Ser Pro Gly Pro Pro Ala Glu Gln Leu Leu Ser Gln
                115                 120                 125

Ala Arg Asp Phe Ile Asn Gln Tyr Tyr Ser Ser Ile Lys Arg Ser Gly
        130                 135                 140

Ser Gln Ala His Glu Glu Arg Leu Gln Glu Val Glu Ala Glu Val Ala
145                 150                 155                 160

Ser Thr Gly Thr Tyr His Leu Arg Glu Ser Glu Leu Val Phe Gly Ala
                165                 170                 175

Lys Gln Ala Trp Arg Asn Ala Pro Arg Cys Val Gly Arg Ile Gln Trp
                180                 185                 190

Gly Lys Leu Gln Val Phe Asp Ala Arg Asp Cys Ser Ser Ala Gln Glu
        195                 200                 205

Met Phe Thr Tyr Ile Cys Asn His Ile Lys Tyr Ala Thr Asn Arg Gly
        210                 215                 220

Asn Leu Arg Ser Ala Ile Thr Val Phe Pro Gln Arg Ala Pro Gly Arg
225                 230                 235                 240

Gly Asp Phe Arg Ile Trp Asn Ser Gln Leu Val Arg Tyr Ala Gly Tyr
                245                 250                 255

Arg Gln Gln Asp Gly Ser Val Arg Gly Asp Pro Ala Asn Val Glu Ile
                260                 265                 270

Thr Glu Leu Cys Ile Gln His Gly Trp Thr Pro Gly Asn Gly Arg Phe
                275                 280                 285

Asp Val Leu Pro Leu Leu Leu Gln Ala Pro Asp Glu Ala Pro Glu Leu
        290                 295                 300

Phe Val Leu Pro Pro Glu Leu Val Leu Glu Val Pro Leu Glu His Pro
```

```
            305                 310                 315                 320

Thr Leu Glu Trp Phe Ala Ala Leu Gly Leu Arg Trp Tyr Ala Leu Pro
                    325                 330                 335

Ala Val Ser Asn Met Leu Leu Glu Ile Gly Gly Leu Glu Phe Ser Ala
                    340                 345                 350

Ala Pro Phe Ser Gly Trp Tyr Met Ser Thr Glu Ile Gly Thr Arg Asn
                    355                 360                 365

Leu Cys Asp Pro His Arg Tyr Asn Ile Leu Glu Asp Val Ala Val Cys
                370                 375                 380

Met Asp Leu Asp Thr Arg Thr Thr Ser Ser Leu Trp Lys Asp Lys Ala
385                 390                 395                 400

Ala Val Glu Ile Asn Leu Ala Val Leu His Ser Phe Gln Leu Ala Lys
                    405                 410                 415

Val Thr Ile Val Asp His His Ala Ala Thr Val Ser Phe Met Lys His
                    420                 425                 430

Leu Asp Asn Glu Gln Lys Ala Arg Gly Gly Cys Pro Ala Asp Trp Ala
                    435                 440                 445

Trp Ile Val Pro Pro Ile Ser Gly Ser Leu Thr Pro Val Phe His Gln
                    450                 455                 460

Glu Met Val Asn Tyr Ile Leu Ser Pro Ala Phe Arg Tyr Gln Pro Asp
465                 470                 475                 480

Pro Trp Lys Gly Ser Ala Thr Lys Gly Ala Gly Ile Thr Arg Lys Lys
                    485                 490                 495

Thr Phe Lys Glu Val Ala Asn Ala Val Lys Ile Ser Ala Ser Leu Met
                    500                 505                 510

Gly Thr Leu Met Ala Lys Arg Val Lys Ala Thr Ile Leu Tyr Ala Ser
                    515                 520                 525

Glu Thr Gly Arg Ala Gln Ser Tyr Ala Gln Gln Leu Gly Arg Leu Phe
                530                 535                 540

Arg Lys Ala Phe Asp Pro Arg Val Leu Cys Met Asp Glu Tyr Asp Val
545                 550                 555                 560

Val Ser Leu Glu His Glu Ala Leu Val Leu Val Val Thr Ser Thr Phe
                    565                 570                 575

Gly Asn Gly Asp Pro Pro Glu Asn Gly Glu Ser Phe Ala Ala Ala Leu
                    580                 585                 590

Met Glu Met Ser Gly Pro Tyr Asn Ser Ser Pro Arg Pro Glu Gln His
                    595                 600                 605

Lys Ser Tyr Lys Ile Arg Phe Asn Ser Val Ser Cys Ser Asp Pro Leu
                    610                 615                 620

Val Ser Ser Trp Arg Arg Lys Arg Lys Glu Ser Ser Asn Thr Asp Ser
625                 630                 635                 640

Ala Gly Ala Leu Gly Thr Leu Arg Phe Cys Val Phe Gly Leu Gly Ser
                    645                 650                 655

Arg Ala Tyr Pro His Phe Cys Ala Phe Ala Arg Ala Val Asp Thr Arg
                    660                 665                 670

Leu Glu Glu Leu Gly Gly Glu Arg Leu Leu Gln Leu Gly Gln Gly Asp
                    675                 680                 685

Glu Leu Cys Gly Gln Glu Glu Ala Phe Arg Gly Trp Ala Lys Ala Ala
                690                 695                 700

Phe Gln Ala Ser Cys Glu Thr Phe Cys Val Gly Glu Glu Ala Lys Ala
705                 710                 715                 720

Ala Ala Gln Asp Ile Phe Ser Pro Lys Arg Ser Trp Lys Arg Gln Arg
                    725                 730                 735
```

-continued

```
Tyr Arg Leu Ser Thr Gln Ala Glu Gly Leu Gln Leu Pro Gly Leu
            740                 745                 750

Ile His Val His Arg Arg Lys Met Phe Gln Ala Thr Val Leu Ser Val
            755                 760                 765

Glu Asn Leu Gln Ser Ser Lys Ser Thr Arg Ala Thr Ile Leu Val Arg
            770                 775                 780

Leu Asp Thr Ala Gly Gln Glu Gly Leu Gln Tyr Gln Pro Gly Asp His
785                 790                 795                 800

Ile Gly Ile Cys Pro Pro Asn Arg Pro Gly Leu Val Glu Ala Leu Leu
                805                 810                 815

Ser Arg Val Glu Asp Pro Pro Pro Thr Glu Ser Val Ala Val Glu
                820                 825                 830

Gln Leu Glu Lys Gly Ser Pro Gly Gly Pro Pro Ser Trp Val Arg
            835                 840                 845

Asp Pro Arg Leu Pro Pro Cys Thr Leu Arg Gln Ala Leu Thr Phe Phe
            850                 855                 860

Leu Asp Ile Thr Ser Pro Pro Ser Pro Arg Leu Arg Leu Leu Ser
865                 870                 875                 880

Thr Leu Ala Glu Glu Pro Ser Glu Gln Gln Glu Leu Glu Thr Leu Ser
                885                 890                 895

Gln Asp Pro Arg Arg Tyr Glu Glu Trp Lys Trp Phe Arg Cys Pro Thr
            900                 905                 910

Leu Leu Glu Val Leu Glu Gln Phe Pro Ser Val Ala Leu Pro Ala Pro
            915                 920                 925

Leu Leu Leu Thr Gln Leu Pro Leu Leu Gln Pro Arg Tyr Tyr Ser Val
            930                 935                 940

Ser Ser Ala Pro Asn Ala His Pro Gly Glu Val His Leu Thr Val Ala
945                 950                 955                 960

Val Leu Ala Tyr Arg Thr Gln Asp Gly Leu Gly Pro Leu His Tyr Gly
                965                 970                 975

Val Cys Ser Thr Trp Leu Ser Gln Leu Lys Thr Gly Asp Pro Val Pro
            980                 985                 990

Cys Phe Ile Arg Gly Ala Pro Ser Phe Arg Leu Pro Pro Asp Pro Tyr
            995                 1000                1005

Val Pro Cys Ile Leu Val Gly Pro Gly Thr Gly Ile Ala Pro Phe Arg
1010                1015                1020

Gly Phe Trp Gln Glu Arg Leu His Asp Ile Glu Ser Lys Gly Leu Gln
1025                1030                1035                1040

Pro Ala Pro Met Thr Leu Val Phe Gly Cys Arg Cys Ser Gln Leu Asp
                1045                1050                1055

His Leu Tyr Arg Asp Glu Val Gln Asp Ala Gln Glu Arg Gly Val Phe
            1060                1065                1070

Gly Arg Val Leu Thr Ala Phe Ser Arg Glu Pro Asp Ser Pro Lys Thr
            1075                1080                1085

Tyr Val Gln Asp Ile Leu Arg Thr Glu Leu Ala Ala Glu Val His Arg
            1090                1095                1100

Val Leu Cys Leu Glu Arg Gly His Met Phe Val Cys Gly Asp Val Thr
1105                1110                1115                1120

Met Ala Thr Ser Val Leu Gln Thr Val Gln Arg Ile Leu Ala Thr Glu
                1125                1130                1135

Gly Asp Met Glu Leu Asp Glu Ala Gly Asp Val Ile Gly Val Leu Arg
            1140                1145                1150

Asp Gln Gln Arg Tyr His Glu Asp Ile Phe Gly Leu Thr Leu Arg Thr
            1155                1160                1165
```

-continued

Gln Glu Val Thr Ser Arg Ile Arg Thr Gln Ser Phe Ser Leu Gln Glu
            1170                1175                1180

Arg His Leu Arg Gly Ala  Val Pro Trp Ala Phe Asp Pro Pro Gly Pro
1185            1190                1195                1200

Asp Thr Pro Gly Pro
            1205

<210> SEQ ID NO 16
<211> LENGTH: 1203
<212> TYPE: PRT
<213> ORGANISM: Homo sapiens
<220> FEATURE:
<221> NAME/KEY: SOURCE
<222> LOCATION: 1..1203
<223> OTHER INFORMATION: /mol_type="protein"
      /organism="Homo sapiens"

<400> SEQUENCE: 16

Met Gly Asn Leu Lys Ser Val Ala Gln Glu Pro Gly Pro Pro Cys Gly
1               5                   10                  15

Leu Gly Leu Gly Leu Gly Leu Gly Cys Gly Lys Gln Gly Pro Ala
            20                  25                  30

Thr Pro Ala Pro Glu Pro Ser Arg Ala Pro Ala Ser Leu Leu Pro Pro
            35                  40                  45

Ala Pro Glu His Ser Pro Ser Ser Pro Leu Thr Gln Pro Pro Glu
50                  55                  60

Gly Pro Lys Phe Pro Arg Val Lys Asn Trp Glu Val Gly Ser Ile Thr
65                  70                  75                  80

Tyr Asp Thr Leu Ser Ala Gln Ala Gln Gln Asp Gly Pro Cys Thr Pro
                85                  90                  95

Arg Arg Cys Leu Gly Ser Leu Val Phe Pro Arg Lys Leu Gln Gly Arg
            100                 105                 110

Pro Ser Pro Gly Pro Pro Ala Pro Glu Gln Leu Leu Ser Gln Ala Arg
            115                 120                 125

Asp Phe Ile Asn Gln Tyr Tyr Ser Ser Ile Lys Arg Ser Gly Ser Gln
130                 135                 140

Ala His Glu Gln Arg Leu Gln Glu Val Glu Ala Glu Val Ala Ala Thr
145                 150                 155                 160

Gly Thr Tyr Gln Leu Arg Glu Ser Glu Leu Val Phe Gly Ala Lys Gln
                165                 170                 175

Ala Trp Arg Asn Ala Pro Arg Cys Val Gly Arg Ile Gln Trp Gly Lys
            180                 185                 190

Leu Gln Val Phe Asp Ala Arg Asp Cys Arg Ser Ala Gln Glu Met Phe
            195                 200                 205

Thr Tyr Ile Cys Asn His Ile Lys Tyr Ala Thr Asn Arg Gly Asn Leu
210                 215                 220

Arg Ser Ala Ile Thr Val Phe Pro Gln Arg Cys Pro Gly Arg Gly Asp
225                 230                 235                 240

Phe Arg Ile Trp Asn Ser Gln Leu Val Arg Tyr Ala Gly Tyr Arg Gln
                245                 250                 255

Gln Asp Gly Ser Val Arg Gly Asp Pro Ala Asn Val Glu Ile Thr Glu
            260                 265                 270

Leu Cys Ile Gln His Gly Trp Thr Pro Gly Asn Gly Arg Phe Asp Val
            275                 280                 285

Leu Pro Leu Leu Leu Gln Ala Pro Asp Glu Pro Pro Glu Leu Phe Leu
    290                 295                 300

-continued

```
Leu Pro Pro Glu Leu Val Leu Glu Val Pro Leu Glu His Pro Thr Leu
305                 310                 315                 320

Glu Trp Phe Ala Ala Leu Gly Leu Arg Trp Tyr Ala Leu Pro Ala Val
                325                 330                 335

Ser Asn Met Leu Leu Glu Ile Gly Gly Leu Glu Phe Pro Ala Ala Pro
            340                 345                 350

Phe Ser Gly Trp Tyr Met Ser Thr Glu Ile Gly Thr Arg Asn Leu Cys
        355                 360                 365

Asp Pro His Arg Tyr Asn Ile Leu Glu Asp Val Ala Val Cys Met Asp
    370                 375                 380

Leu Asp Thr Arg Thr Thr Ser Ser Leu Trp Lys Asp Lys Ala Ala Val
385                 390                 395                 400

Glu Ile Asn Val Ala Val Leu His Ser Tyr Gln Leu Ala Lys Val Thr
                405                 410                 415

Ile Val Asp His His Ala Ala Thr Ala Ser Phe Met Lys His Leu Glu
            420                 425                 430

Asn Glu Gln Lys Ala Arg Gly Gly Cys Pro Ala Asp Trp Ala Trp Ile
        435                 440                 445

Val Pro Pro Ile Ser Gly Ser Leu Thr Pro Val Phe His Gln Glu Met
    450                 455                 460

Val Asn Tyr Phe Leu Ser Pro Ala Phe Arg Tyr Gln Pro Asp Pro Trp
465                 470                 475                 480

Lys Gly Ser Ala Ala Lys Gly Thr Gly Ile Thr Arg Lys Thr Phe
                485                 490                 495

Lys Glu Val Ala Asn Ala Val Lys Ile Ser Ala Ser Leu Met Gly Thr
            500                 505                 510

Val Met Ala Lys Arg Val Lys Ala Thr Ile Leu Tyr Gly Ser Glu Thr
        515                 520                 525

Gly Arg Ala Gln Ser Tyr Ala Gln Gln Leu Gly Arg Leu Phe Arg Lys
    530                 535                 540

Ala Phe Asp Pro Arg Val Leu Cys Met Asp Glu Tyr Asp Val Val Ser
545                 550                 555                 560

Leu Glu His Glu Thr Leu Val Leu Val Val Thr Ser Thr Phe Gly Asn
                565                 570                 575

Gly Asp Pro Pro Glu Asn Gly Glu Ser Phe Ala Ala Ala Leu Met Glu
            580                 585                 590

Met Ser Gly Pro Tyr Asn Ser Ser Pro Arg Pro Glu Gln His Lys Ser
        595                 600                 605

Tyr Lys Ile Arg Phe Asn Ser Ile Ser Cys Ser Asp Pro Leu Val Ser
    610                 615                 620

Ser Trp Arg Arg Lys Arg Lys Glu Ser Ser Asn Thr Asp Ser Ala Gly
625                 630                 635                 640

Ala Leu Gly Thr Leu Arg Phe Cys Val Phe Gly Leu Gly Ser Arg Ala
                645                 650                 655

Tyr Pro His Phe Cys Ala Phe Ala Arg Ala Val Asp Thr Arg Leu Glu
            660                 665                 670

Glu Leu Gly Gly Glu Arg Leu Leu Gln Leu Gly Gln Gly Asp Glu Leu
        675                 680                 685

Cys Gly Gln Glu Glu Ala Phe Arg Gly Trp Ala Gln Ala Ala Phe Gln
    690                 695                 700

Ala Ala Cys Glu Thr Phe Cys Val Gly Glu Asp Ala Lys Ala Ala Ala
705                 710                 715                 720

Arg Asp Ile Phe Ser Pro Lys Arg Ser Trp Lys Arg Gln Arg Tyr Arg
                725                 730                 735
```

```
Leu Ser Ala Gln Ala Glu Gly Leu Gln Leu Leu Pro Gly Leu Ile His
                740                 745                 750

Val His Arg Arg Lys Met Phe Gln Ala Thr Ile Arg Ser Val Glu Asn
                755                 760                 765

Leu Gln Ser Ser Lys Ser Thr Arg Ala Thr Ile Leu Val Arg Leu Asp
        770                 775                 780

Thr Gly Gly Gln Glu Gly Leu Gln Tyr Gln Pro Gly Asp His Ile Gly
785                 790                 795                 800

Val Cys Pro Pro Asn Arg Pro Gly Leu Val Glu Ala Leu Leu Ser Arg
                805                 810                 815

Val Glu Asp Pro Pro Ala Pro Thr Glu Pro Val Ala Val Glu Gln Leu
                820                 825                 830

Glu Lys Gly Ser Pro Gly Gly Pro Pro Pro Gly Trp Val Arg Asp Pro
                835                 840                 845

Arg Leu Pro Pro Cys Thr Leu Arg Gln Ala Leu Thr Phe Phe Leu Asp
        850                 855                 860

Ile Thr Ser Pro Pro Ser Pro Gln Leu Leu Arg Leu Leu Ser Thr Leu
865                 870                 875                 880

Ala Glu Glu Pro Arg Glu Gln Gln Glu Leu Glu Ala Leu Ser Gln Asp
                885                 890                 895

Pro Arg Arg Tyr Glu Glu Trp Lys Trp Phe Arg Cys Pro Thr Leu Leu
                900                 905                 910

Glu Val Leu Glu Gln Phe Pro Ser Val Ala Leu Pro Ala Pro Leu Leu
                915                 920                 925

Leu Thr Gln Leu Pro Leu Leu Gln Pro Arg Tyr Tyr Ser Val Ser Ser
        930                 935                 940

Ala Pro Ser Thr His Pro Gly Glu Ile His Leu Thr Val Ala Val Leu
945                 950                 955                 960

Ala Tyr Arg Thr Gln Asp Gly Leu Gly Pro Leu His Tyr Gly Val Cys
                965                 970                 975

Ser Thr Trp Leu Ser Gln Leu Lys Pro Gly Asp Pro Val Pro Cys Phe
                980                 985                 990

Ile Arg Gly Ala Pro Ser Phe Arg Leu Pro Pro Asp Pro Ser Leu Pro
                995                 1000                1005

Cys Ile Leu Val Gly Pro Gly Thr Gly Ile Ala Pro Phe Arg Gly Phe
        1010                1015                1020

Trp Gln Glu Arg Leu His Asp Ile Glu Ser Lys Gly Leu Gln Pro Thr
1025                1030                1035                1040

Pro Met Thr Leu Val Phe Gly Cys Arg Cys Ser Gln Leu Asp His Leu
                1045                1050                1055

Tyr Arg Asp Glu Val Gln Asn Ala Gln Gln Arg Gly Val Phe Gly Arg
                1060                1065                1070

Val Leu Thr Ala Phe Ser Arg Glu Pro Asp Asn Pro Lys Thr Tyr Val
                1075                1080                1085

Gln Asp Ile Leu Arg Thr Glu Leu Ala Ala Glu Val His Arg Val Leu
        1090                1095                1100

Cys Leu Glu Arg Gly His Met Phe Val Cys Gly Asp Val Thr Met Ala
1105                1110                1115                1120

Thr Asn Val Leu Gln Thr Val Gln Arg Ile Leu Ala Thr Glu Gly Asp
                1125                1130                1135

Met Glu Leu Asp Glu Ala Gly Asp Val Ile Gly Val Leu Arg Asp Gln
                1140                1145                1150

Gln Arg Tyr His Glu Asp Ile Phe Gly Leu Thr Leu Arg Thr Gln Glu
```

```
                1155                1160                1165
Val Thr Ser Arg Ile Arg Thr Gln Ser Phe Ser Leu Gln Glu Arg Gln
                1170                1175                1180

Leu Arg Gly Ala Val Pro Trp Ala Phe Asp Pro Pro Gly Ser Asp Thr
1185                1190                1195                1200

Asn Ser Pro

<210> SEQ ID NO 17
<211> LENGTH: 4
<212> TYPE: PRT
<213> ORGANISM: Bos taurus
<220> FEATURE:
<221> NAME/KEY: SOURCE
<222> LOCATION: 1..4
<223> OTHER INFORMATION: /mol_type="protein"
      /organism="Bos taurus"

<400> SEQUENCE: 17

Pro Trp Ala Phe
1

<210> SEQ ID NO 18
<211> LENGTH: 4
<212> TYPE: PRT
<213> ORGANISM: Bos taurus
<220> FEATURE:
<221> NAME/KEY: SOURCE
<222> LOCATION: 1..4
<223> OTHER INFORMATION: /mol_type="protein"
      /organism="Bos taurus"

<400> SEQUENCE: 18

Gly Ala Val Pro
1

<210> SEQ ID NO 19
<211> LENGTH: 21
<212> TYPE: PRT
<213> ORGANISM: Bos taurus
<220> FEATURE:
<221> NAME/KEY: SOURCE
<222> LOCATION: 1..21
<223> OTHER INFORMATION: /mol_type="protein"
      /organism="Bos taurus"

<400> SEQUENCE: 19

Arg His Leu Arg Gly Ala Val Pro Trp Ala Phe Asp Pro Pro Gly Pro
1               5                   10                  15

Asp Thr Pro Gly Pro
            20

<210> SEQ ID NO 20
<211> LENGTH: 12
<212> TYPE: PRT
<213> ORGANISM: Bos taurus
<220> FEATURE:
<221> NAME/KEY: SOURCE
<222> LOCATION: 1..12
<223> OTHER INFORMATION: /mol_type="protein"
      /organism="Bos taurus"

<400> SEQUENCE: 20

Ala Phe Asp Pro Pro Gly Pro Asp Thr Pro Gly Pro
1               5                   10

<210> SEQ ID NO 21
<211> LENGTH: 11
```

```
<212> TYPE: PRT
<213> ORGANISM: Bos taurus
<220> FEATURE:
<221> NAME/KEY: SOURCE
<222> LOCATION: 1..11
<223> OTHER INFORMATION: /mol_type="protein"
      /organism="Bos taurus"

<400> SEQUENCE: 21

His Leu Arg Gly Ala Val Pro Trp Ala Phe Asp
1               5                   10

<210> SEQ ID NO 22
<211> LENGTH: 20
<212> TYPE: PRT
<213> ORGANISM: Bos taurus
<220> FEATURE:
<221> NAME/KEY: SOURCE
<222> LOCATION: 1..20
<223> OTHER INFORMATION: /mol_type="protein"
      /organism="Bos taurus"

<400> SEQUENCE: 22

His Leu Arg Gly Ala Val Pro Trp Ala Phe Asp Pro Pro Gly Pro Asp
1               5                   10                  15

Thr Pro Gly Pro
            20
```

PHARMACEUTICAL COMPOSITIONS COMPRISING ACTIVATED-POTENTIATED ANTIBODIES TO HUMAN INSULIN RECEPTOR AND ENDOTHELIAL NITRIC OXIDE (NO) SYNTHASE

FIELD

The present invention relates to the field of medicine and can be used for the treatment and prevention of diseases of the diabetes and other metabolic disorders.

BACKGROUND

Diabetes Mellitus is a chronic condition characterized as hyperglycemia (high levels of sugar in blood). Continuing increments of blood glucose levels increase the risk of diabetes-related complications such as kidney damage, vision loss, heart disease, and foot ulcers.

There are two major types of diabetes: type 1 diabetes and type 2 diabetes. With type 1 diabetes, hyperglycemia develops because the pancreas cannot produce insulin. This type of diabetes usually appears in childhood or young adulthood. In type 2 diabetes, the pancreas is capable of producing insulin, but it cannot adequately meet the body's demands. The problem is that the body does not respond to the insulin appropriately, which in turn leads to less glucose being absorbed by the cells and results in abnormally elevated blood glucose levels. After overworking the pancreas for a number of years, the pancreas may eventually fail and exhaust its ability to produce insulin, which at this point a person with type 2 diabetes may require insulin therapy.

Insulin, a natural hormone produced by the pancreas, transports glucose from the bloodstream to the inside of the cells. Thus, the main job of insulin is to regulate the glucose transport into the cells thereby lowering the level of blood glucose.

The actions of insulin are controlled through the activation of a heterotetrameric receptor which is found in the plasma membrane. The insulin receptor is a glycoprotein composed of two extracellular alpha-subunits and two transmembrane beta-subunits linked by disulfide bonds. Ullrich et al., Nature, 313:756-61, 1985. The alpha-subunits contain the insulin-binding domain, and the intracellular portion of the beta-subunit contains the insulin-regulated tyrosine protein kinase (the enzyme that catalyzes the transfer of a high-energy group from a donor (usually ATP) to an acceptor).

When an insulin molecule is released by the beta cells of the pancreas and arrives at a cell, it binds onto the insulin receptor on the surface of most cells. Once insulin binds, the intrinsic phosphotransferase function of the insulin receptor beta-subunit is activated, resulting in the tyrosine phosphorylation of a number of intracellular proteins. Once the insulin receptor has been activated, the phosphorylation event leads to an increase in glucose storage and consequently a decrease in blood glucose levels.

Effective control of glucose level is difficult to achieve for prolonged periods even with the most meticulous mode of insulin therapy in the most motivated patients. Thus, there is a continuing need for new drug products with desired therapeutic efficacy for treatment of diseases and metabolic disorders.

Nitric oxide (NO) is a gaseous molecule that has been shown to acts in the signaling of different biological processes. Endothelium-derived NO is a key molecule in regulation of vascular tone and its association with vascular disease has long been recognized. NO inhibits many processes known to be involved in the formation of atherosclerotic plaque, including monocyte adhesion, platelet aggregation and vascular smooth muscle cell proliferation. Another important role of endothelial NO is the protection of the vascular wall from the oxidative stress induced by its own metabolic products and by the oxidation products of lipids and lipoproteins. Endothelial dysfunction occurs at very early stages of atherosclerosis. It is therefore possible that deficiency in local NO availability could be a final common pathway that accelerates atherogenesis in humans. In addition to its role in the vascular endothelium, NO availability has been shown to modulate metabolism of lipoproteins. Negative correlation has been reported between plasma concentrations of NO metabolic products and plasma total and Low Density Lipoprotein [LDL] cholesterol levels while High Density Lipoprotein [HDL] improves vascular function in hypercholesterolaemic subjects. The loss of NO has considerable effect on the development of the disease. Diabetes mellitus is associated with increased rates of morbidity and mortality caused primarily by the accelerated development of atherosclerotic disease. Moreover, reports show that diabetics have impaired lung functions. It has been proposed that insulin resistance leads to airway inflammation. Habib et al., *Nitric Oxide Measurement From Blood To Lungs, Is There A Link?* Pak J Physiol 2007; 3(1).

Nitric oxide is synthesized by the endothelium from L-arginine by nitric oxide synthase (NO synthase). NO synthase occurs in different isoforms, including a constitutive form (cNOS) and an inducible form (iNOS). The constitutive form is present in normal endothelial cells, neurons and some other tissues.

The therapeutic effect of an extremely diluted (or ultra-low) form of antibodies potentized by homeopathic technology has been discovered by the inventor of the present patent application, Dr. Oleg I. Epshtein. U.S. Pat. No. 7,582,294 discloses a medicament for treating Benign Prostatic Hyperplasia or prostatitis by administration of a homeopathically activated form of antibodies to prostate specific antigen (PSA). U.S. Pat. No. 7,700,096 discloses a homeopathically potentized form of antibodies to endothelial NO-synthase. The homepathically potentized form of antibodies to endothelial NO-synthase is marketed in the Russian Federation and other countries under the name IMPAZA®.

SUMMARY

In one aspect, the invention provides a pharmaceutical composition for administration to a patient suffering from diseases of diabetes and other metabolic disorders, the composition comprises a) an activated-potentiated form of an antibody to human insulin receptor, and b) an activated-potentiated form of an antibody to endothelial NO-synthase.

In one aspect, the invention provides a pharmaceutical composition for administration to a patient suffering from diseases of diabetes and other metabolic disorders, the composition comprises a) an activated-potentiated form of an antibody to a C-terminal fragment of the beta subunit of human insulin receptor, and b) an activated-potentiated form of an antibody to endothelial NO-synthase.

In one variant, the pharmaceutical composition of this aspect of the invention comprises a) an activated-potentiated form of an antibody to human insulin receptor, and b) an activated-potentiated form of an antibody to endothelial NO-synthase, wherein the insulin receptor molecule comprises at least one alpha subunit and at least one beta subunit.

In one variant, the pharmaceutical composition of this aspect of the invention includes activated-potentiated form of an antibody to a C-terminal fragment of the beta subunit of human insulin receptor or the activated-potentiated form of an antibody to human insulin receptor in the form of a mixture of C12, C30, and C200 homeopathic dilutions impregnated onto a solid carrier. The activated-potentiated form of an antibody to endothelial NO-synthase in the form of mixture of C12, C30, and C200 homeopathic dilutions may be subsequently impregnated onto the solid carrier.

In another variant, the pharmaceutical composition of this aspect of the invention includes the activated-potentiated form of an antibody to endothelial NO-synthase is in the form of mixture of C12, C30, and C200 homeopathic dilutions impregnated onto a solid carrier. The activated-potentiated form of an antibody to a C-terminal fragment of the beta subunit of human insulin receptor or the activated-potentiated form of an antibody to human insulin receptor is in the form of mixture of C12, C30, and C200 homeopathic dilutions may be subsequently impregnated onto the solid carrier.

Preferably, the activated-potentiated form of an antibody to a C-terminal fragment of the beta subunit of human insulin receptor or the activated-potentiated form of an antibody to human insulin receptor is a monoclonal, polyclonal or natural antibody, more preferably, a polyclonal antibody. In one variant of this aspect of the invention, the activated-potentiated form of an antibody to a C-terminal fragment of the beta subunit of human insulin receptor or the activated-potentiated form of an antibody to human insulin receptor is prepared by successive centesimal dilutions coupled with shaking of every dilution.

Preferably, the activated-potentiated form of an antibody to endothelial NO-synthase is a monoclonal, polyclonal or natural antibody, more preferably, a polyclonal antibody. In one variant of this aspect of the invention, the activated-potentiated form of an antibody to endothelial NO-synthase is prepared by successive centesimal dilutions coupled with shaking of every dilution.

In another aspect, the invention provides a method of treating a patient suffering from Type I, diabetes, the method comprising administering to the patient a combination of a) an activated-potentiated form of an antibody to human insulin receptor, and b) an activated-potentiated form of an antibody to endothelial NO-synthase.

In another aspect, the invention provides a method of treating a patient suffering from Type I diabetes, the method comprising administering to the patient a combination of a) an activated-potentiated form of an antibody to a C-terminal fragment of the beta subunit of human insulin receptor, and b) an activated-potentiated form of an antibody to endothelial NO-synthase.

In another aspect, the invention provides a method of treating a patient suffering from Type II, diabetes, the method comprising administering to the patient a combination of a) an activated-potentiated form of an antibody to human insulin receptor, and b) an activated-potentiated form of an antibody to endothelial NO-synthase.

In another aspect, the invention provides a method of treating a patient suffering from Type II diabetes, the method comprising administering to the patient a combination of a) an activated-potentiated form of an antibody to a C-terminal fragment of the beta subunit of human insulin receptor, and b) an activated-potentiated form of an antibody to endothelial NO-synthase.

In another aspect, the invention provides a method of reducing blood glucose level in a mammal, the method comprising administering to the mammal a combination of a) an activated-potentiated form of an antibody to human insulin receptor, and b) an activated-potentiated form of an antibody to endothelial NO-synthase.

In another aspect, the invention provides a method of reducing blood glucose level in a mammal, the method comprising administering to the mammal a combination of a) an activated-potentiated form of an antibody to a C-terminal fragment of the beta subunit of human insulin receptor, and b) an activated-potentiated form of an antibody to endothelial NO-synthase.

In another aspect, the invention provides a method of treating insulin resistance in a mammal, the method comprising administering to the mammal a combination of a) an activated-potentiated form of an antibody to human insulin receptor, and b) an activated-potentiated form of an antibody to endothelial NO-synthase.

In another aspect, the invention provides a method of treating insulin resistance in a mammal, the method comprising administering to the mammal a combination of a) an activated-potentiated form of an antibody to a C-terminal fragment of the beta subunit of human insulin receptor, and b) an activated-potentiated form of an antibody to endothelial NO-synthase.

In one variant of this aspect of the invention, there is provided administration of from one to two unit dosage forms of the activated-potentiated form of an antibody to a C-terminal fragment of the beta subunit of human insulin receptor or an activated-potentiated form of an antibody to human insulin receptor, and from one to two unit dosage forms of the activated-potentiated form of an antibody to endothelial NO-synthase, each of the dosage form being administered from once daily to four times daily. Preferably, the one to two unit dosage forms of each of the activated-potentiated forms of antibodies is administered twice daily.

DETAILED DESCRIPTION

Figure 1:
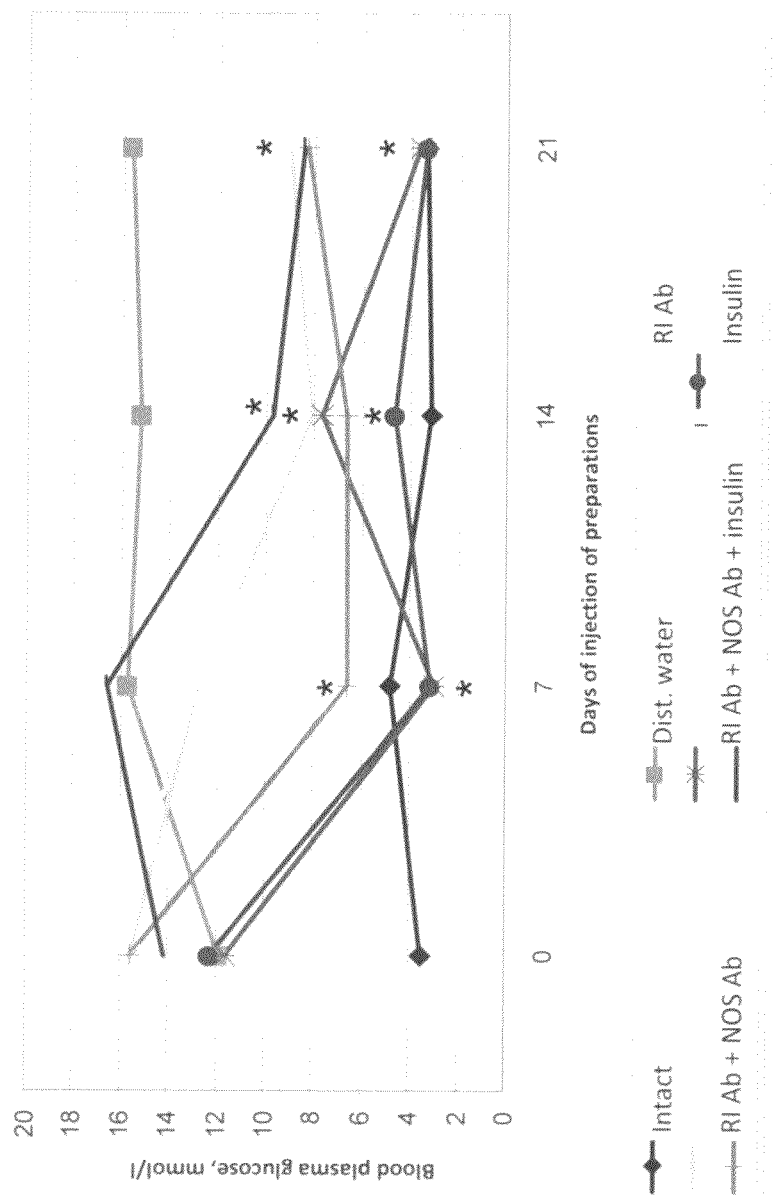
FIG. 1—Illustrates the effect of tested preparations on blood plasma glucose level of rats with streptozotocin-induced diabetes mellitus FIG. 2—Illustrates the effect of tested preparations on day 14 of injection on indicators of area under concentration-time curve (AUC) in the glucose tolerance test in rats with streptozotocin-induced diabetes mellitus.

The invention is defined with reference to the appended claims. With respect to the claims, the glossary that follows provides the relevant definitions.

The term "antibody" as used herein shall mean an immunoglobulin that specifically binds to, and is thereby defined as complementary with, a particular spatial and polar organization of another molecule. Antibodies as recited in the claims may include a complete immunoglobulin or fragment thereof, may be natural, polyclonal or monoclonal, and may include various classes and isotypes, such as IgA, IgD, IgE, IgG1, IgG2a, IgG2b and IgG3, IgM, etc. Fragments thereof may include Fab, Fv and F(ab')2, Fab', and the like. The singular "antibody" includes plural "antibodies."

The term "activated-potentiated form" or "potentiated form" respectively, with respect to antibodies recited herein is used to denote a product of homeopathic potentization of any initial solution of antibodies. "Homeopathic potentization" denotes the use of methods of homeopathy to impart homeopathic potency to an initial solution of relevant substance. Although not so limited, 'homeopathic potentization" may involve, for example, repeated consecutive dilutions combined with external treatment, particularly (mechanical) shaking. In other words, an initial solution of antibody is subjected to consecutive repeated dilution and multiple vertical shaking of each obtained solution in accordance with homeopathic technology. The preferred concentration of the initial solution of antibody in the solvent, preferably water or a water-ethyl alcohol mixture, ranges from about 0.5 to about 5.0 mg/ml. The preferred procedure for preparing each component, i.e. antibody solution, is the use of the mixture of three aqueous or aqueous-alcohol dilutions of the primary matrix solution (mother tincture) of antibodies diluted $100^{12}$, $100^{30}$ and $100^{200}$ times, respectively, which is equivalent to centesimal homeopathic dilutions (C12, C30, and C200) or the use of the mixture of three aqueous or aqueous-alcohol dilutions of the primary matrix solution of antibodies diluted $100^{12}$, $100^{30}$ and $100^{50}$ times, respectively, which is equivalent to centesimal homeopathic dilutions (C12, C30 and C50). Examples of homeopathic potentization are described in U.S. Pat. Nos. 7,572,441 and 7,582,294, which are incorporated herein by reference in their entirety and for the purpose stated. While the term "activated-potentiated form" is used in the claims, the term "ultra-low doses" is used in the examples. The term "ultra-low doses" became a term of art in the field of art created by study and use of homeopathically diluted and potentized form of substance. The term "ultra-low dose" or "ultra-low doses" is meant as fully supportive and primarily synonymous with the term 'activated-potentiated" form used in the claims.

In other words, an antibody is in the "activated-potentiated" form when three factors are present. First, the "activated-potentiated" form of the antibody is a product of a preparation process well accepted in the homeopathic art. Second, the "activated-potentiated" form of antibody must have biological activity determined by methods well accepted in modern pharmacology. And third, the biological activity exhibited by the "activated potentiated" form of the antibody cannot be explained by the presence of the molecular form of the antibody in the final product of the homeopathic process.

For example, the activated potentiated form of antibodies may be prepared by subjecting an initial, isolated antibody in a molecular form to consecutive multiple dilutions coupled with an external impact, such as mechanical shaking. The external treatment in the course of concentration reduction may also be accomplished, for example, by exposure to ultrasonic, electromagnetic, or other physical factors. V. Schwabe "Homeopathic medicines", M., 1967, U.S. Pat. Nos. 7,229,648 and 4,311,897, which are incorporated by reference in their entirety and for the purpose stated, describe such processes that are well accepted methods of homeopathic potentiation in the homeopathic art. This procedure gives rise to a uniform decrease in molecular concentration of the initial molecular form of the antibody. This procedure is repeated until the desired homeopathic potency is obtained. For the individual antibody, the required homeopathic potency can be determined by subjecting the intermediate dilutions to biological testing in the desired pharmacological model.

Although not so limited, 'homeopathic potentization" may involve, for example, repeated consecutive dilutions combined with external treatment, particularly vertical (mechanical) shaking. In other words, an initial solution of antibody is subjected to consecutive repeated dilution and multiple vertical shaking of each obtained solution in accordance with homeopathic technology. The preferred concentration of the initial solution of antibody in the solvent, preferably, water or a water-ethyl alcohol mixture, ranges from about 0.5 to about 5.0 mg/ml. The preferred procedure for preparing each component, i.e. antibody solution, is the use of the mixture of three aqueous or aqueous-alcohol dilutions of the primary matrix solution (mother tincture) of antibodies diluted $100^{12}$, $100^{30}$ and $100^{200}$ times, respectively, which is equivalent to centesimal homeopathic dilutions C12, C30 and C200 or the mixture of three aqueous or aqueous-alcohol dilutions of the primary matrix solution (mother tincture) of antibodies diluted $100^{12}$, $100^{30}$ and $100^{50}$ times, respectively, which is equivalent to centesimal homeopathic dilutions C12, C30 and C50. Examples of how to obtain the desired potency are also provided, for example, in U.S. Pat. Nos. 7,229,648 and 4,311,897, which are incorporated by reference for the purpose stated. The procedure applicable to the "activated potentiated" form of the antibodies described herein is described in more detail below.

There has been a considerable amount of controversy regarding homeopathic treatment of human subjects. While the present invention relies on accepted homeopathic processes to obtain the "activated-potentiated" form of antibodies, it does not rely solely on homeopathy in human subjects for evidence of activity. It has been surprisingly discovered by the inventor of the present application and amply demonstrated in the accepted pharmacological models that the solvent ultimately obtained from consecutive multiple dilution of a starting molecular form of an antibody has definitive activity unrelated to the presence of the traces of the molecular form of the antibody in the target dilution. The "activated-potentiated" form of the antibody provided herein are tested for biological activity in well accepted pharmacological models of activity, either in appropriate in vitro experiments, or in vivo in suitable animal models. The experiments provided further below provide evidence of biological activity in such models. The human clinical studies, also provided herein below, are evidence, inter alia, that the activity observed in the animal model are well translated to human therapy. The human study also provide evidence of availability of the "activated potentiated" forms described herein to treat specified human diseases or disorders well accepted as pathological conditions in the medical science.

Also, the claimed "activated-potentiated" form of antibody encompass only solutions or solid preparations the biological activity of which cannot be explained by the presence of the molecular form of the antibody remaining from the initial, starting solution. In other words, while it is contemplated that the "activated-potentiated" form of the antibody may contain traces of the initial molecular form of the antibody, one skilled in the art could not attribute the observed biological activity in the accepted pharmacological models to the remaining molecular form of the antibody with any degree of plausibility due to the extremely low concentrations of the molecular form of the antibody remaining after the consecutive dilutions. While the invention is not limited by any specific theory, the biological activity of the "activated-potentiated' form of the antibodies of the present invention is not attributable to the initial molecular form of the antibody. Preferred is the "activated-potentiated" form of antibody in liquid or solid form in which the concentration of the initial molecular form of the antibody is below the limit of detection of the accepted analytical techniques, such as capillary electrophoresis and High Performance Liquid Chromatography. Particularly preferred is the "activated-potentiated" form of antibody in liquid or solid form in which the concentration of the initial molecular form of the antibody is below the Avogadro number. In pharmacology of molecular forms of therapeutic substances, it is common practice to create a dose-response curve in which the level of pharmacological response is plotted against the concentration of the active drug administered to the subject or tested in vitro. The minimal level of the drug which produces any detectable response is known as a threshold dose. It is specifically contemplated and preferred that the "activated-potentiated" form of the antibodies contains molecular antibody, if any, at a concentration below the threshold dose for the molecular form of the antibody in the given biological model.

The present invention provides a pharmaceutical composition for administration to a patient suffering from diseases of diabetes and other metabolic disorders, comprising a) an activated-potentiated form of an antibody to a C-terminal fragment of the beta subunit of human insulin receptor or an activated-potentiated form of an antibody to human insulin receptor and b) an activated-potentiated form of an antibody to endothelial NO-synthase. As set forth herein above, each of the individual components of the combination is generally known for its own individual medical uses. However, the inventors of the present patent application surprisingly discovered that administration of the combination is useful in treating a patient with diabetes and insulin resistance and further reduces blood glucose levels. While applicant is not bound by this theory, the "accelerator" hypothesis assumes that type I diabetes mellitus (DM) and type II diabetes mellitus are the same disease characterized by insulin resistance, whose development into type I DM and type II DM is determined by the patient's genotype. This hypothesis does not deny the role of autoimmune processes; however, it casts doubt on its primary role. The "accelerator" hypothesis divides type I and type II diabetes mellitus according to the speed of progression: in with type I diabetes, rapid development of pathological changes determines the earlier onset of the manifestations of clinical disease symptoms. The hypothesis was proposed for the first time in 2001 and at present is confirmed by the results of 6 independent clinical trials (see Wilkin, T. J. The accelerator hypothesis: a review of the evidence for insulin resistance as the basis for type [I] as well as type II diabetes. //International Journal for Obesity. 2009: Vol. 33-p. 716-726.). A key role in the pathogenesis of both types of diabetes is played by insulin resistance, which decrease leads to alleviation of the clinical course of both type I diabetes and type II diabetes (see Cellular mechanisms of insulin resistance. World Congress on Insulin Resistance Syndrome, 2009, Diabetes Care. 2010: Vol. 33, N8, pp. 103-108.). The role of the insulin receptor beta subunit in the insulin signal path is known. After insulin binding with the receptor and beta subunit activation, the path can go into two different directions: phosphatidylinositol 3-kinase (PI 3-K) or MAP kinase (MAP-K).

The first path appears to be necessary for realization of the majority of the metabolic and antiapoptotic effects of insulin, and the alternate path is connected with its non-metabolic, proliferative and mitogenic effects. In insulin resistance, it has been shown that only metabolic insulin resistance, linked with the beta subunit activation along the P13-K pathway, plays an important role in determining the development of diabetes mellitus. (See Muntoni, S, Muntoni, S. *Insulin Resistance: Pathophysiology and Rationale for Treatment*, Ann. Nutr. Metab. 2011: Vol. 58, N1, pp. 25-36). The claimed pharmaceutical composition ensures an effect on metabolic insulin resistance.

The pharmaceutical composition in accordance with this aspect of the invention may be in the liquid form or in solid form. Each of the activated potentiated forms of the antibodies included in the pharmaceutical composition is prepared from an initial molecular form of the antibody via a process accepted in homeopathic art. The starting antibodies may be monoclonal, or polyclonal antibodies prepared in accordance with known processes, for example, as described in *Immunotechniques*, G. Frimel, M., "Meditsyna", 1987, p. 9-33; "*Hum. Antibodies. Monoclonal and recombinant antibodies, 30 years after*" by Laffly E., Sodoyer R.—2005—Vol. 14.—N 1-2. P. 33-55, both incorporated herein by reference.

Monoclonal antibodies may be obtained, e.g., by means of hybridoma technology. The initial stage of the process includes immunization based on the principles already developed in course of polyclonal antisera preparation. Further stages of work involve production of hybrid cells generating clones of antibodies with identical specificity. Their separate isolation is performed using the same methods as in case of polyclonal antisera preparation.

Polyclonal antibodies may be obtained via active immunization of animals. For this purpose, for example, suitable animals (e.g. rabbits) receive a series of injections of the appropriate antigen, either endothelial NO-synthase and C-terminal fragment of the beta subunit of human insulin receptor or endothelial NO-synthase and human insulin receptor. The animals' immune system generates corresponding antibodies, which are collected from the animals in a known manner. This procedure enables preparation of a monospecific antibody-rich serum. If desired, the serum containing antibodies may be purified, e.g., using affine chromatography, fractionation by salt precipitation, or ion-exchange chromatography. The resulting purified, antibody-enriched serum may be used as a starting material for preparation of the activated-potentiated form of the antibodies. The preferred concentration of the resulting initial solution of antibody in the solvent, preferably, water or water-ethyl alcohol mixture, ranges from about 0.5 to about 5.0 mg/ml.

The preferred procedure for preparing each component is the use of the mixture of three aqueous-alcohol dilutions of the primary matrix solution of antibodies diluted $100^{12}$, $100^{30}$ and $100^{200}$ times, respectively, which is equivalent to centesimal homeopathic dilutions C12, C30 and C200. To prepare a solid dosage form, a solid carrier is treated with the desired dilution obtained via the homeopathic process. To obtain a solid unit dosage form of the combination of the invention, the carrier mass is impregnated with each of the dilutions. Both orders of impregnation are suitable to prepare the desired combination dosage form.

In the preferred embodiment, the starting material for the preparation of the activated potentiated form that comprise the combination of the invention is polyclonal, animal-raised antibody to the corresponding antigen, namely, C-terminal fragment of beta subunit of human insulin receptor or human insulin receptor and endothelial NO-synthase. To obtain the activated-potentiated form of polyclonal antibodies to C-terminal fragment of beta subunit of human insulin receptor, the desired antigen may be injected as immunogen into a laboratory animal, preferably, rabbits'. Peptides of particular interest may include at least about 3 amino acids, usually at least about 10 on either side of the sequence, preferably having at least 3 amino acids at the C-terminal side. The following sequences of human insulin receptor are specifically contemplated as suitable antigens:

Entire Alpha-Subunit of Human Insulin Receptor:

SEQ ID NO: 1

```
                                        His Leu Tyr
                                         28      30

Pro Gly Glu Val Cys Pro Gly Met Asp Ile Arg Asn Asn Leu Thr
 31          35              40                      45

Arg Leu His Glu Leu Glu Asn Cys Ser Val Ile Glu Gly His Leu
 46          50              55                      60

Gln Ile Leu Leu Met Phe Lys Thr Arg Pro Glu Asp Phe Arg Asp
 61          65              70                      75

Leu Ser Phe Pro Lys Leu Ile Met Ile Thr Asp Tyr Leu Leu Leu
 76          80              85                      90

Phe Arg Val Tyr Gly Leu Glu Ser Leu Lys Asp Leu Phe Pro Asn
 91          95             100                     105

Leu Thr Val Ile Arg Gly Ser Arg Leu Phe Phe Asn Tyr Ala Leu
106         110             115                     120

Val Ile Phe Glu Met Val His Leu Lys Glu Leu Gly Leu Tyr Asn
121         125             130                     135

Leu Met Asn Ile Thr Arg Gly Ser Val Arg Ile Glu Lys Asn Asn
136         140             145                     150

Glu Leu Cys Tyr Leu Ala Thr Ile Asp Trp Ser Arg Ile Leu Asp
151         155             160                     165

Ser Val Glu Asp Asn Tyr Ile Val Leu Asn Lys Asp Asp Asn Glu
166         170             175                     180

Glu Cys Gly Asp Ile Cys Pro Gly Thr Ala Lys Gly Lys Thr Asn
181         185             190                     195

Cys Pro Ala Thr Val Ile Asn Gly Gln Phe Val Glu Arg Cys Trp
196         200             205                     210

Thr His Ser His Cys Gln Lys Val Cys Pro Thr Ile Cys Lys Ser
211         215             220                     225

His Gly Cys Thr Ala Glu Gly Leu Cys Cys His Ser Glu Cys Leu
226         230             235                     240

Gly Asn Cys Ser Gln Pro Asp Asp Pro Thr Lys Cys Val Ala Cys
241         245             250                     255

Arg Asn Phe Tyr Leu Asp Gly Arg Cys Val Glu Thr Cys Pro Pro
256         260             265                     270

Pro Tyr Tyr His Phe Gln Asp Trp Arg Cys Val Asn Phe Ser Phe
271         275             280                     285

Cys Gln Asp Leu His His Lys Cys Lys Asn Ser Arg Arg Gln Gly
286         290             295                     300

Cys His Gln Tyr Val Ile His Asn Asn Lys Cys Ile Pro Glu Cys
301         305             310                     315

Pro Ser Gly Tyr Thr Met Asn Ser Ser Asn Leu Leu Cys Thr Pro
316         320             325                     330

Cys Leu Gly Pro Cys Pro Lys Val Cys His Leu Leu Glu Gly Glu
331         335             340                     345

Lys Thr Ile Asp Ser Val Thr Ser Ala Gln Glu Leu Arg Gly Cys
346         350             355                     360

Thr Val Ile Asn Gly Ser Leu Ile Ile Asn Ile Arg Gly Gly Asn
361         365             370                     375

Asn Leu Ala Ala Glu Leu Glu Ala Asn Leu Gly Leu Ile Glu Glu
376         380             385                     390

Ile Ser Gly Tyr Leu Lys Ile Arg Arg Ser Tyr Ala Leu Val Ser
391         395             400                     405
```

```
Leu Ser Phe Phe Arg Lys Leu Arg Leu Ile Arg Gly Glu Thr Leu
406                 410                 415                 420

Glu Ile Gly Asn Tyr Ser Phe Tyr Ala Leu Asp Asn Gln Asn Leu
421                 425                 430                 435

Arg Gln Leu Trp Asp Trp Ser Lys His Asn Leu Thr Ile Thr Gln
436                 440                 445                 450

Gly Lys Leu Phe Phe His Tyr Asn Pro Lys Leu Cys Leu Ser Glu
451                 455                 460                 465

Ile His Lys Met Glu Glu Val Ser Gly Thr Lys Gly Arg Gln Glu
466                 470                 475                 480

Arg Asn Asp Ile Ala Leu Lys Thr Asn Gly Asp Gln Ala Ser Cys
481                 485                 490                 495

Glu Asn Glu Leu Leu Lys Phe Ser Tyr Ile Arg Thr Ser Phe Asp
496                 500                 505                 510

Lys Ile Leu Leu Arg Trp Glu Pro Tyr Trp Pro Pro Asp Phe Arg
511                 515                 510                 525

Asp Leu Leu Gly Phe Met Leu Phe Tyr Lys Glu Ala Pro Tyr Gln
526                 530                 535                 540

Asn Val Thr Glu Phe Asp Gly Gln Asp Ala Cys Gly Ser Asn Ser
541                 545                 550                 555

Trp Thr Val Val Asp Ile Asp Pro Pro Leu Arg Ser Asn Asp Pro
556                 560                 565                 570

Lys Ser Gln Asn His Pro Gly Trp Leu Met Arg Gly Leu Lys Pro
571                 575                 580                 585

Trp Thr Gln Tyr Ala Ile Phe Val Lys Thr Leu Val Thr Phe Ser
586                 590                 595                 600

Asp Glu Arg Arg Thr Tyr Gly Ala Lys Ser Asp Ile Ile Tyr Val
601                 605                 610                 615

Gln Thr Asp Ala Thr Asn Pro Ser Val Pro Leu Asp Pro Ile Ser
616                 620                 625                 630

Val Ser Asn Ser Ser Gln Ile Ile Leu Lys Trp Lys Pro Pro
631                 635                 640                 645

Ser Asp Pro Asn Gly Asn Ile Thr His Tyr Leu Val Phe Trp Glu
646                 650                 655                 660

Arg Gln Ala Glu Asp Ser Glu Leu Phe Glu Leu Asp Tyr Cys Leu
661                 665                 670                 675

Lys Gly Leu Lys Leu Pro Ser Arg Thr Trp Ser Pro Pro Phe Glu
676                 680                 685                 690

Ser Glu Asp Ser Gln Lys His Asn Gln Ser Glu Tyr Glu Asp Ser
691                 695                 700                 705

Ala Gly Glu Cys Cys Ser Cys Pro Lys Thr Asp Ser Gln Ile Leu
706                 710                 715                 720

Lys Glu Leu Glu Glu Ser Ser Phe Arg Lys Thr Phe Glu Asp Tyr
721                 725                 730                 735

Leu His Asn Val Val Phe Val Pro Arg Lys Thr Ser Ser Gly Thr
736                 740                 745                 750

Gly Ala Glu Asp Pro Arg Pro Ser Arg Lys Arg Arg
751                 755                 760     762
```

Fragments of Alpha-Subunit of Human Insulin Receptor:

```
                                        SEQ ID NO: 2
                        Leu Gly Leu Tyr Asn
                        131             135
Leu Met Asn Ile Thr Arg Gly Ser Val
136             140         144
                                        SEQ ID NO: 3
                        Lys Gly Lys Thr Asn
                        191             195
Cys Pro Ala Thr Val Ile Asn Gly
196             200     203
                                        SEQ ID NO: 4
                Trp Ser Lys His Asn Leu Thr Ile Thr Gln
                441             445                 450
Gly Lys Leu
451     453
                                        SEQ ID NO: 5
Asn Val Thr Glu Phe Asp Gly Gln Asp Ala Cys Gly Ser Asn Ser
541             545             550                 555
Trp Thr Val Val Asp
556         560
                                        SEQ ID NO: 6
                        Asp Ile Ile Tyr Val
                        611             615
Gln Thr Asp Ala Thr
616         620
                                        SEQ ID NO: 7
                            Tyr Glu Asp Ser
                            702         705
Ala Gly Glu Cys Cys Ser Cys Pro Lys Thr Asp Ser Gln Ile
706             710             715             719
```

Entire Beta Subunit of Human Insulin Receptor:

```
                                        SEQ ID NO: 8
                                    Ser Leu Gly
                                    763     765
Asp Val Gly Asn Val Thr Val Ala Val Pro Thr Val Ala Ala Phe
766             770             775              780
Pro Asn Thr Ser Ser Thr Ser Val Pro Thr Ser Pro Glu Glu His
781             785             790              795
Arg Pro Phe Glu Lys Val Val Asn Lys Glu Ser Leu Val Ile Ser
796             800             805              810
Gly Leu Arg His Phe Thr Gly Tyr Arg Ile Glu Leu Gln Ala Cys
811             815             820              825
Asn Gln Asp Thr Pro Glu Glu Arg Cys Ser Val Ala Ala Tyr Val
826             830             835              840
Ser Ala Arg Thr Met Pro Glu Ala Lys Ala Asp Asp Ile Val Gly
841             845             850              855
Pro Val Thr His Glu Ile Phe Glu Asn Asn Val Val His Leu Met
856             860             865              870
Trp Gln Glu Pro Lys Glu Pro Asn Gly Leu Ile Val Leu Tyr Glu
871             875             880              885
Val Ser Tyr Arg Arg Tyr Gly Asp Glu Glu Leu His Leu Cys Val
886             890             895              900
Ser Arg Lys His Phe Ala Leu Glu Arg Gly Cys Arg Leu Arg Gly
901             905             910              915
```

-continued

```
Leu Ser Pro Gly Asn Tyr Ser Val Arg Ile Arg Ala Thr Ser Leu
916                 920                 925                 930

Ala Gly Asn Gly Ser Trp Thr Glu Pro Thr Tyr Phe Tyr Val Thr
931                 935                 940                 945

Asp Tyr Leu Asp Val Pro Ser Asn Ile Ala Lys Ile Ile Ile Gly
946                 950                 955                 960

Pro Leu Ile Phe Val Phe Leu Phe Ser Val Val Ile Gly Ser Ile
961                 965                 970                 975

Tyr Leu Phe Leu Arg Lys Arg Gln Pro Asp Gly Pro Leu Gly Pro
976                 980                 985                 990

Leu Tyr Ala Ser Ser Asn Pro Glu Tyr Leu Ser Ala Ser Asp Val
991                 995                 1000                1005

Phe Pro Cys Ser Val Tyr Val Pro Asp Glu Trp Glu Val Ser Arg
1006                1010                1015                1020

Glu Lys Ile Thr Leu Leu Arg Glu Leu Gly Gln Gly Ser Phe Gly
1021                1025                1030                1035

Met Val Tyr Glu Gly Asn Ala Arg Asp Ile Ile Lys Gly Glu Ala
1036                1140                1145                1050

Glu Thr Arg Val Ala Val Lys Thr Val Asn Glu Ser Ala Ser Leu
1051                1155                1160                1065

Arg Glu Arg Ile Glu Phe Leu Asn Glu Ala Ser Val Met Lys Gly
1066                1170                1175                1080

Phe Thr Cys His His Val Val Arg Leu Leu Gly Val Val Ser Lys
1081                1185                1190                1095

Gly Gln Pro Thr Leu Val Val Met Glu Leu Met Ala His Gly Asp
1096                1100                1105                1110

Leu Lys Ser Tyr Leu Arg Ser Leu Arg Pro Glu Ala Glu Asn Asn
1111                1115                1120                1125

Pro Gly Arg Pro Pro Thr Leu Gln Glu Met Ile Gln Met Ala
1126                1130                1135                1140

Ala Glu Ile Ala Asp Gly Met Ala Tyr Leu Asn Ala Lys Lys Phe
1141                1145                1150                1155

Val His Arg Asp Leu Ala Ala Arg Asn Cys Met Val Ala His Asp
1156                1160                1165                1170

Phe Thr Val Lys Ile Gly Asp Phe Gly Met Thr Arg Asp Ile Tyr
1171                1175                1180                1185

Glu Thr Asp Tyr Tyr Arg Lys Gly Gly Lys Gly Leu Leu Pro Val
1186                1190                1195                1200

Arg Trp Met Ala Pro Glu Ser Leu Lys Asp Gly Val Phe Thr Thr
1201                1205                1210                1215

Ser Ser Asp Met Trp Ser Phe Gly Val Val Leu Trp Glu Ile Thr
1216                1220                1225                1230

Ser Leu Ala Glu Gln Pro Tyr Gln Gly Leu Ser Asn Glu Gln Val
1231                1235                1240                1245

Leu Lys Phe Val Met Asp Gly Gly Tyr Leu Asp Gln Pro Asp Asn
1246                1250                1255                1260

Cys Pro Glu Arg Val Thr Asp Leu Met Arg Met Cys Trp Gln Phe
1261                1265                1270                1275

Asn Pro Lys Met Arg Pro Thr Phe Leu Glu Ile Val Asn Leu Leu
1276                1280                1285                1290

Lys Asp Asp Leu His Pro Ser Phe Pro Glu Val Ser Phe Phe His
1291                1295                1300                1305

Ser Glu Glu Asn Lys Ala Pro Glu Ser Glu Glu Leu Glu Met Glu
1306                1310                1315                1320
```

-continued

```
Phe Glu Asp Met Glu Asn Val Pro Leu Asp Arg Ser Ser His Cys
1321            1325            1330            1335

Gln Arg Glu Glu Ala Gly Gly Arg Asp Gly Gly Ser Ser Leu Gly
1336            1340            1345            1350

Phe Lys Arg Ser Tyr Glu Glu His Ile Pro Tyr Thr His Met Asn
1351            1355            1360            1365

Gly Gly Lys Lys Asn Gly Arg Ile Leu Thr Leu Pro Arg Ser Asn
1366            1370            1375            1380

Pro Ser
13811382
```

Fragments of C-Terminal Fragment of Beta Subunit of [15] Human Insulin Receptor:

```
                                                SEQ ID NO: 9
Lys Lys Asn Gly Arg Ile Leu Thr Leu Pro
1368    1370            1375    1377

SEQ ID NO: 10
                Arg Ile Leu Thr Leu Pro Arg Ser Asn
                1372            1375            1380

Pro Ser
13811382
                                                SEQ ID NO: 11
Lys Asn Gly Arg Ile Leu Thr
13691370            1375

SEQ ID NO: 12
Gly Gly Lys Lys Asn Gly Arg Ile Leu Thr Leu Pro Arg Ser Asn
1366            1370            1375            1380

Pro Ser
13811382
                                                SEQ ID NO: 13
                                                        Asn
                                                        1365

Gly Gly Lys Lys Asn Gly Arg Ile Leu Thr Leu Pro Arg Ser Asn
1366            1370            1375            1380

Pro Ser
13811382
```

The use of human insulin receptor as antigen is also contemplated. The suitable sequence for such antigen is as follow:

```
                                                SEQ ID NO: 14
Met Ala Thr Gly Gly Arg Arg Gly Ala Ala Ala Ala Pro Leu Leu
 1              5               10              15

Val Ala Val Ala Ala Leu Leu Leu Gly Ala Ala Gly His Leu Tyr
16              20              25              30

Pro Gly Glu Val Cys Pro Gly Met Asp Ile Arg Asn Asn Leu Thr
31              35              40              45

Arg Leu His Glu Leu Glu Asn Cys Ser Val Ile Glu Gly His Leu
46              50              55              60

Gln Ile Leu Leu Met Phe Lys Thr Arg Pro Glu Asp Phe Arg Asp
61              65              70              75

Leu Ser Phe Pro Lys Leu Ile Met Ile Thr Asp Tyr Leu Leu Leu
76              80              85              90

Phe Arg Val Tyr Gly Leu Glu Ser Leu Lys Asp Leu Phe Pro Asn
91              95              100             105
```

```
Leu Thr Val Ile Arg Gly Ser Arg Leu Phe Phe Asn Tyr Ala Leu
106                 110                 115                 120

Val Ile Phe Glu Met Val His Leu Lys Glu Leu Gly Leu Tyr Asn
121                 125                 130                 135

Leu Met Asn Ile Thr Arg Gly Ser Val Arg Ile Glu Lys Asn Asn
136                 140                 145                 150

Glu Leu Cys Tyr Leu Ala Thr Ile Asp Trp Ser Arg Ile Leu Asp
151                 155                 160                 165

Ser Val Glu Asp Asn Tyr Ile Val Leu Asn Lys Asp Asp Asn Glu
166                 170                 175                 180

Glu Cys Gly Asp Ile Cys Pro Gly Thr Ala Lys Gly Lys Thr Asn
181                 185                 190                 195

Cys Pro Ala Thr Val Ile Asn Gly Gln Phe Val Glu Arg Cys Trp
196                 200                 205                 210

Thr His Ser His Cys Gln Lys Val Cys Pro Thr Ile Cys Lys Ser
211                 215                 220                 225

His Gly Cys Thr Ala Glu Gly Leu Cys Cys His Ser Glu Cys Leu
226                 230                 235                 240

Gly Asn Cys Ser Gln Pro Asp Asp Pro Thr Lys Cys Val Ala Cys
241                 245                 250                 255

Arg Asn Phe Tyr Leu Asp Gly Arg Cys Val Glu Thr Cys Pro Pro
256                 260                 265                 270

Pro Tyr Tyr His Phe Gln Asp Trp Arg Cys Val Asn Phe Ser Phe
271                 275                 280                 285

Cys Gln Asp Leu His His Lys Cys Lys Asn Ser Arg Arg Gln Gly
286                 290                 295                 300

Cys His Gln Tyr Val Ile His Asn Asn Lys Cys Ile Pro Glu Cys
301                 305                 310                 315

Pro Ser Gly Tyr Thr Met Asn Ser Ser Asn Leu Leu Cys Thr Pro
316                 320                 325                 330

Cys Leu Gly Pro Cys Pro Lys Val Cys His Leu Leu Glu Gly Glu
331                 335                 340                 345

Lys Thr Ile Asp Ser Val Thr Ser Ala Gln Glu Leu Arg Gly Cys
346                 350                 355                 360

Thr Val Ile Asn Gly Ser Leu Ile Ile Asn Ile Arg Gly Gly Asn
361                 365                 370                 375

Asn Leu Ala Ala Glu Leu Glu Ala Asn Leu Gly Leu Ile Glu Glu
376                 380                 385                 390

Ile Ser Gly Tyr Leu Lys Ile Arg Arg Ser Tyr Ala Leu Val Ser
391                 395                 400                 405

Leu Ser Phe Phe Arg Lys Leu Arg Leu Ile Arg Gly Glu Thr Leu
406                 410                 415                 420

Glu Ile Gly Asn Tyr Ser Phe Tyr Ala Leu Asp Asn Gln Asn Leu
421                 425                 430                 435

Arg Gln Leu Trp Asp Trp Ser Lys His Asn Leu Thr Ile Thr Gln
436                 440                 445                 450

Gly Lys Leu Phe Phe His Tyr Asn Pro Lys Leu Cys Leu Ser Glu
451                 455                 460                 465

Ile His Lys Met Glu Glu Val Ser Gly Thr Lys Gly Arg Gln Glu
466                 470                 475                 480

Arg Asn Asp Ile Ala Leu Lys Thr Asn Gly Asp Gln Ala Ser Cys
481                 485                 490                 495

Glu Asn Glu Leu Leu Lys Phe Ser Tyr Ile Arg Thr Ser Phe Asp
496                 500                 505                 510
```

-continued

```
Lys Ile Leu Leu Arg Trp Glu Pro Tyr Trp Pro Asp Phe Arg
511                 515                 510                 525

Asp Leu Leu Gly Phe Met Leu Phe Tyr Lys Glu Ala Pro Tyr Gln
526                 530                 535                 540

Asn Val Thr Glu Phe Asp Gly Gln Asp Ala Cys Gly Ser Asn Ser
541                 545                 550                 555

Trp Thr Val Val Asp Ile Asp Pro Leu Arg Ser Asn Asp Pro
556                 560                 565                 570

Lys Ser Gln Asn His Pro Gly Trp Leu Met Arg Gly Leu Lys Pro
571                 575                 580                 585

Trp Thr Gln Tyr Ala Ile Phe Val Lys Thr Leu Val Thr Phe Ser
586                 590                 595                 600

Asp Glu Arg Arg Thr Tyr Gly Ala Lys Ser Asp Ile Ile Tyr Val
601                 605                 610                 615

Gln Thr Asp Ala Thr Asn Pro Ser Val Pro Leu Asp Pro Ile Ser
616                 620                 625                 630

Val Ser Asn Ser Ser Gln Ile Ile Leu Lys Trp Lys Pro Pro
631                 635                 640                 645

Ser Asp Pro Asn Gly Asn Ile Thr His Tyr Leu Val Phe Trp Glu
646                 650                 655                 660

Arg Gln Ala Glu Asp Ser Glu Leu Phe Glu Leu Asp Tyr Cys Leu
661                 665                 670                 675

Lys Gly Leu Lys Leu Pro Ser Arg Thr Trp Ser Pro Pro Phe Glu
676                 680                 685                 690

Ser Glu Asp Ser Gln Lys His Asn Gln Ser Glu Tyr Glu Asp Ser
691                 695                 700                 705

Ala Gly Glu Cys Cys Ser Cys Pro Lys Thr Asp Ser Gln Ile Leu
706                 710                 715                 720

Lys Glu Leu Glu Glu Ser Ser Phe Arg Lys Thr Phe Glu Asp Tyr
721                 725                 730                 735

Leu His Asn Val Val Phe Val Pro Arg Lys Thr Ser Ser Gly Thr
736                 740                 745                 750

Gly Ala Glu Asp Pro Arg Pro Ser Arg Lys Arg Arg Ser Leu Gly
751                 755                 760                 765

Asp Val Gly Asn Val Thr Val Ala Val Pro Thr Val Ala Ala Phe
766                 770                 775                 780

Pro Asn Thr Ser Ser Thr Ser Val Pro Thr Ser Pro Glu Glu His
781                 785                 790                 795

Arg Pro Phe Glu Lys Val Val Asn Lys Glu Ser Leu Val Ile Ser
796                 800                 805                 810

Gly Leu Arg His Phe Thr Gly Tyr Arg Ile Glu Leu Gln Ala Cys
811                 815                 820                 825

Asn Gln Asp Thr Pro Glu Glu Arg Cys Ser Val Ala Ala Tyr Val
826                 830                 835                 840

Ser Ala Arg Thr Met Pro Glu Ala Lys Ala Asp Asp Ile Val Gly
841                 845                 850                 855

Pro Val Thr His Glu Ile Phe Glu Asn Asn Val Val His Leu Met
856                 860                 865                 870

Trp Gln Glu Pro Lys Glu Pro Asn Gly Leu Ile Val Leu Tyr Glu
871                 875                 880                 885

Val Ser Tyr Arg Arg Tyr Gly Asp Glu Glu Leu His Leu Cys Val
886                 890                 895                 900

Ser Arg Lys His Phe Ala Leu Glu Arg Gly Cys Arg Leu Arg Gly
901                 905                 910                 915
```

-continued

```
Leu Ser Pro Gly Asn Tyr Ser Val Arg Ile Arg Ala Thr Ser Leu
916                 920                 925                 930

Ala Gly Asn Gly Ser Trp Thr Glu Pro Thr Tyr Phe Tyr Val Thr
931                 935                 940                 945

Asp Tyr Leu Asp Val Pro Ser Asn Ile Ala Lys Ile Ile Ile Gly
946                 950                 955                 960

Pro Leu Ile Phe Val Phe Leu Phe Ser Val Val Ile Gly Ser Ile
961                 965                 970                 975

Tyr Leu Phe Leu Arg Lys Arg Gln Pro Asp Gly Pro Leu Gly Pro
976                 980                 985                 990

Leu Tyr Ala Ser Ser Asn Pro Glu Tyr Leu Ser Ala Ser Asp Val
991                 995                 1000                1005

Phe Pro Cys Ser Val Tyr Val Pro Asp Glu Trp Glu Val Ser Arg
1006                1010                1015                1020

Glu Lys Ile Thr Leu Leu Arg Glu Leu Gly Gln Gly Ser Phe Gly
1021                1025                1030                1035

Met Val Tyr Glu Gly Asn Ala Arg Asp Ile Ile Lys Gly Glu Ala
1036                1140                1145                1050

Glu Thr Arg Val Ala Val Lys Thr Val Asn Glu Ser Ala Ser Leu
1051                1155                1160                1065

Arg Glu Arg Ile Glu Phe Leu Asn Glu Ala Ser Val Met Lys Gly
1066                1170                1175                1080

Phe Thr Cys His His Val Val Arg Leu Leu Gly Val Val Ser Lys
1081                1185                1190                1095

Gly Gln Pro Thr Leu Val Val Met Glu Leu Met Ala His Gly Asp
1096                1100                1105                1110

Leu Lys Ser Tyr Leu Arg Ser Leu Arg Pro Glu Ala Glu Asn Asn
1111                1115                1120                1125

Pro Gly Arg Pro Pro Thr Leu Gln Glu Met Ile Gln Met Ala
1126                1130                1135                1140

Ala Glu Ile Ala Asp Gly Met Ala Tyr Leu Asn Ala Lys Lys Phe
1141                1145                1150                1155

Val His Arg Asp Leu Ala Ala Arg Asn Cys Met Val Ala His Asp
1156                1160                1165                1170

Phe Thr Val Lys Ile Gly Asp Phe Gly Met Thr Arg Asp Ile Tyr
1171                1175                1180                1185

Glu Thr Asp Tyr Tyr Arg Lys Gly Gly Lys Gly Leu Leu Pro Val
1186                1190                1195                1200

Arg Trp Met Ala Pro Glu Ser Leu Lys Asp Gly Val Phe Thr Thr
1201                1205                1210                1215

Ser Ser Asp Met Trp Ser Phe Gly Val Val Leu Trp Glu Ile Thr
1216                1220                1225                1230

Ser Leu Ala Glu Gln Pro Tyr Gln Gly Leu Ser Asn Glu Gln Val
1231                1235                1240                1245

Leu Lys Phe Val Met Asp Gly Gly Tyr Leu Asp Gln Pro Asp Asn
1246                1250                1255                1260

Cys Pro Glu Arg Val Thr Asp Leu Met Arg Met Cys Trp Gln Phe
1261                1265                1270                1275

Asn Pro Lys Met Arg Pro Thr Phe Leu Glu Ile Val Asn Leu Leu
1276                1280                1285                1290

Lys Asp Asp Leu His Pro Ser Phe Pro Glu Val Ser Phe Phe His
1291                1295                1300                1305

Ser Glu Glu Asn Lys Ala Pro Glu Ser Glu Glu Leu Glu Met Glu
1306                1310                1315                1320
```

-continued

```
Phe Glu Asp Met Glu Asn Val Pro Leu Asp Arg Ser Ser His Cys
1321        1325            1330            1335

Gln Arg Glu Glu Ala Gly Gly Arg Asp Gly Gly Ser Ser Leu Gly
1336        1340            1345            1350

Phe Lys Arg Ser Tyr Glu Glu His Ile Pro Tyr Thr His Met Asn
1351        1355            1360            1365

Gly Gly Lys Lys Asn Gly Arg Ile Leu Thr Leu Pro Arg Ser Asn
1366        1370            1375            1380

Pro Ser
13811382
```

The exemplary procedure for preparation of the starting polyclonal antibodies to C-terminal fragment of beta subunit of human insulin receptor may be described as follows. In 7-9 days before blood sampling, 1-3 intravenous injections of the desired antigen are made to the rabbits to increase the level of polyclonal antibodies in the rabbit blood stream. Upon immunization, blood samples are taken to test the antibody level. Typically, the maximum level of immune reaction of the soluble antigen is achieved within 40 to 60 days after the first injection of the antigen. Upon completion of the first immunization cycle, rabbits have a 30-day rehabilitation period, after which re-immunization is performed with another 1-3 intravenous injections.

To obtain antiserum containing the desired antibodies, the immunized rabbits' blood is collected from rabbits and placed in 50 ml centrifuge tube. Product clots formed on the tube sides are removed with a wooden spatula, and a rod is placed into the clot in the tube center. The blood is then placed in a refrigerator for one night at the temperature of about 40° C. On the following day, the clot on the spatula is removed, and the remaining liquid is centrifuged for 10 min at 13,000 rotations. Supernatant fluid is the target antiserum. The obtained antiserum is typically yellow. 20% of NaN$_3$ (weight concentration) is added in the antiserum to the final concentration of 0.02% and stored before use in frozen state at the temperature of −20° C. (or without NaN$_3$ at the temperature of −70° C.). To separate the target antibodies to C-terminal fragment of beta subunit of human insulin-receptor from the antiserum, the following solid phase absorption sequence is suitable:

10 ml of the antiserum of rabbits is diluted twofold with 0.15 M NaCl, after which 6.26 g Na$_2$SO$_4$ is added, mixed and incubated for 12-16 hours at 4° C. The sediment is removed by centrifugation, diluted in 10 ml of phosphate buffer and dialyzed against the same buffer during one night at ambient temperature. After the sediment is removed, the solution is applied to DEAE-cellulose column balanced by phosphate buffer. The antibody fraction is determined by measuring the optical density of eluate at 280 Nm.

The isolated crude antibodies are purified using the affine chromatography method by attaching the obtained antibodies to a C-terminal fragment of beta subunit of human insulin receptor located on the insoluble matrix of the chromatography media, with subsequent elution by concentrated aqueous salt solutions.

The resulting buffer solution is used as the initial solution for the homeopathic dilution process used to prepare the activated potentiated form of the antibodies. The preferred concentration of the initial matrix solution of the antigen-purified polyclonal rabbit antibodies to C-terminal fragment of beta subunit of human insulin-receptor is 0.5 to 5.0 mg/ml, preferably, 2.0 to 3.0 mg/ml.

The polyclonal antibodies to endothelial NO-synthase are obtained by a similar methodology using the adjuvant. In order to obtain polyclonal antibodies to endothelial NO-synthase, it is possible to use the entire molecule of bovine endothelial NO-synthase of the below-described sequence as immunogen (antigen):

```
                                                      SEQ ID NO: 15
Met Gly Asn Leu Lys Ser Val Gly Gln Glu Pro Gly Pro Pro Cys
1               5               10              15

Gly Leu Gly Leu Gly Leu Gly Leu Gly Leu Cys Gly Lys Gln Gly
16              20              25              30

Pro Ala Ser Pro Ala Pro Glu Pro Ser Arg Ala Pro Ala Pro Ala
31              35              40              45

Thr Pro His Ala Pro Asp His Ser Pro Ala Pro Asn Ser Pro Thr
46              50              55              60

Leu Thr Arg Pro Pro Glu Gly Pro Lys Phe Pro Arg Val Lys Asn
61              65              70              75

Trp Glu Leu GLys er Ile Thr Tyr Asp Thr Leu Cys Ala Gln Ser
76              80              85              90

Gln Gln Asp Gly Pro Cys Thr Pro Arg Cys Cys Leu GLys er Leu
91              95              100             105

Val Leu Pro Arg Lys Leu Gln Thr Arg Pro Ser Pro Gly Pro Pro
106             110             115             120

Pro Ala Glu Gln Leu Leu Ser Gln Ala Arg Asp Phe Ile Asn Gln
121             125             130             135
```

```
Tyr Tyr Ser Ser Ile Lys Arg Ser GLys er Gln Ala His Glu Glu
136                 140                 145                 150

Arg Leu Gln Glu Val Glu Ala Glu Val Ala Ser Thr Gly Thr Tyr
151                 155                 160                 165

His Leu Arg Glu Ser Glu Leu Val Phe Gly Ala Lys Gln Ala Trp
166                 170                 175                 180

Arg Asn Ala Pro Arg Cys Val Gly Arg Ile Gln Trp Gly Lys Leu
181                 185                 190                 195

Gln Val Phe Asp Ala Arg Asp Cys Ser Ser Ala Gln Glu Met Phe
196                 200                 205                 210

Thr Tyr Ile Cys Asn His Ile Lys Tyr Ala Thr Asn Arg Gly Asn
211                 215                 220                 225

Leu Arg Ser Ala Ile Thr Val Phe Pro Gln Arg Ala Pro Gly Arg
226                 230                 235                 240

Gly Asp Phe Arg Ile Trp Asn Ser Gln Leu Val Arg Tyr Ala Gly
241                 245                 250                 255

Tyr Arg Gln Gln Asp GLys er Val Arg Gly Asp Pro Ala Asn Val
256                 260                 265                 270

Glu Ile Thr Glu Leu Cys Ile Gln His Gly Trp Thr Pro Gly Asn
271                 275                 280                 285

Gly Arg Phe Asp Val Leu Pro Leu Leu Leu Gln Ala Pro Asp Glu
286                 290                 295                 300

Ala Pro Glu Leu Phe Val Leu Pro Pro Glu Leu Val Leu Glu Val
301                 305                 310                 315

Pro Leu Glu His Pro Thr Leu Glu Trp Phe Ala Ala Leu Gly Leu
316                 320                 325                 330

Arg Trp Tyr Ala Leu Pro Ala Val Ser Asn Met Leu Leu Glu Ile
331                 335                 340                 345

Gly Gly Leu Glu Phe Ser Ala Ala Pro Phe Ser Gly Trp Tyr Met
346                 350                 355                 360

Ser Thr Glu Ile Gly Thr Arg Asn Leu Cys Asp Pro His Arg Tyr
361                 365                 370                 375

Asn Ile Leu Glu Asp Val Ala Val Cys Met Asp Leu Asp Thr Arg
376                 380                 385                 390

Thr Thr Ser Ser Leu Trp Lys Asp Lys Ala Ala Val Glu Ile Asn
391                 395                 400                 405

Leu Ala Val Leu His Ser Phe Gln Leu Ala Lys Val Thr Ile Val
406                 410                 415                 420

Asp His His Ala Ala Thr Val Ser Phe Met Lys His Leu Asp Asn
421                 425                 430                 435

Glu Gln Lys Ala Arg Gly Gly Cys Pro Ala Asp Trp Ala Trp Ile
436                 440                 445                 450

Val Pro Pro Ile Ser GLys er Leu Thr Pro Val Phe His Gln Glu
451                 455                 460                 465

Met Val Asn Tyr Ile Leu Ser Pro Ala Phe Arg Tyr Gln Pro Asp
466                 470                 475                 480

Pro Trp Lys GLy Ser Ala Thr Lys Gly Ala Gly Ile Thr Arg Lys
481                 485                 490                 495

Lys Thr Phe Lys Glu Val Ala Asn Ala Val Lys Ile Ser Ala Ser
496                 500                 505                 510

Leu Met Gly Thr Leu Met Ala Lys Arg Val Lys Ala Thr Ile Leu
511                 515                 510                 525

Tyr Ala Ser Glu Thr Gly Arg Ala Gln Ser Tyr Ala Gln Gln Leu
526                 530                 535                 540
```

```
Gly Arg Leu Phe Arg Lys Ala Phe Asp Pro Arg Val Leu Cys Met
541                 545                 550                 555

Asp Glu Tyr Asp Val Val Ser Leu Glu His Glu Ala Leu Val Leu
556                 560                 565                 570

Val Val Thr Ser Thr Phe Gly Asn Gly Asp Pro Pro Glu Asn Gly
571                 575                 580                 585

Glu Ser Phe Ala Ala Ala Leu Met Glu Met Ser Gly Pro Tyr Asn
586                 590                 595                 600

Ser Ser Pro Arg Pro Glu Gln His Lys Ser Tyr Lys Ile Arg Phe
601                 605                 610                 615

Asn Ser Val Ser Cys Ser Asp Pro Leu Val Ser Ser Trp Arg Arg
616                 620                 625                 630

Lys Arg Lys Glu Ser Ser Asn Thr Asp Ser Ala Gly Ala Leu Gly
631                 635                 640                 645

Thr Leu Arg Phe Cys Val Phe Gly Leu GLy Ser Arg Ala Tyr Pro
646                 650                 655                 660

His Phe Cys Ala Phe Ala Arg Ala Val Asp Thr Arg Leu Glu Glu
661                 665                 670                 675

Leu Gly Gly Glu Arg Leu Leu Gln Leu Gln Gly Asp Glu Leu
676                 680                 685                 690

Cys Gly Gln Glu Glu Ala Phe Arg Gly Trp Ala Lys Ala Ala Phe
691                 695                 700                 705

Gln Ala Ser Cys Glu Thr Phe Cys Val Gly Glu Ala Lys Ala
706                 710                 715                 720

Ala Ala Gln Asp Ile Phe Ser Pro Lys Arg Ser Trp Lys Arg Gln
721                 725                 730                 735

Arg Tyr Arg Leu Ser Thr Gln Ala Glu Gly Leu Gln Leu Leu Pro
736                 740                 745                 750

Gly Leu Ile His Val His Arg Arg Lys Met Phe Gln Ala Thr Val
751                 755                 760                 765

Leu Ser Val Glu Asn Leu Gln Ser Ser Lys Ser Thr Arg Ala Thr
766                 770                 775                 780

Ile Leu Val Arg Leu Asp Thr Ala Gly Gln Glu Gly Leu Gln Tyr
781                 785                 790                 795

Gln Pro Gly Asp His Ile Gly Ile Cys Pro Pro Asn Arg Pro Gly
796                 800                 805                 810

Leu Val Glu Ala Leu Leu Ser Arg Val Glu Asp Pro Pro Pro
811                 815                 820                 825

Thr Glu Ser Val Ala Val Glu Gln Leu Glu Lys GLys er Pro Gly
826                 830                 835                 840

Gly Pro Pro Pro Ser Trp Val Arg Asp Pro Arg Leu Pro Pro Cys
841                 845                 850                 855

Thr Leu Arg Gln Ala Leu Thr Phe Phe Leu Asp Ile Thr Ser Pro
856                 860                 865                 870

Pro Ser Pro Arg Leu Leu Arg Leu Leu Ser Thr Leu Ala Glu Glu
871                 875                 880                 885

Pro Ser Glu Gln Gln Glu Leu Glu Thr Leu Ser Gln Asp Pro Arg
886                 890                 895                 900

Arg Tyr Glu Glu Trp Lys Trp Phe Arg Cys Pro Thr Leu Leu Glu
901                 905                 910                 915

Val Leu Glu Gln Phe Pro Ser Val Ala Leu Pro Ala Pro Leu Leu
916                 920                 925                 930

Leu Thr Gln Leu Pro Leu Leu Gln Pro Arg Tyr Tyr Ser Val Ser
931                 935                 940                 945
```

-continued

```
Ser Ala Pro Asn Ala His Pro Gly Glu Val His Leu Thr Val Ala
946             950                 955                 960

Val Leu Ala Tyr Arg Thr Gln Asp Gly Leu Gly Pro Leu His Tyr
961             965                 970                 975

Gly Val Cys Ser Thr Trp Leu Ser Gln Leu Lys Thr Gly Asp Pro
976             980                 985                 990

Val Pro Cys Phe Ile Arg Gly Ala Pro Ser Phe Arg Leu Pro Pro
991             995                 1000                1005

Asp Pro Tyr Val Pro Cys Ile Leu Val Gly Pro Gly Thr Gly Ile
1006            1010                1015                1020

Ala Pro Phe Arg Gly Phe Trp Gln Glu Arg Leu His Asp Ile Glu
1021            1025                1030                1035

Ser Lys Gly Leu Gln Pro Ala Pro Met Thr Leu Val Phe Gly Cys
1036            1040                1045                1050

Arg Cys Ser Gln Leu Asp His Leu Tyr Arg Asp Glu Val Gln Asp
1051            1055                1060                1065

Ala Gln Glu Arg Gly Val Phe Gly Arg Val Leu Thr Ala Phe Ser
1066            1070                1075                1080

Arg Glu Pro Asp Ser Pro Lys Thr Tyr Val Gln Asp Ile Leu Arg
1081            1085                1090                1095

Thr Glu Leu Ala Ala Glu Val His Arg Val Leu Cys Leu Glu Arg
1096            1100                1105                1110

Gly His Met Phe Val Cys Gly Asp Val Thr Met Ala Thr Ser Val
1111            1115                1120                1125

Leu Gln Thr Val Gln Arg Ile Leu Ala Thr Glu Gly Asp Met Glu
1126            1130                1135                1140

Leu Asp Glu Ala Gly Asp Val Ile Gly Val Leu Arg Asp Gln Gln
1141            1145                1150                1155

Arg Tyr His Glu Asp Ile Phe Gly Leu Thr Leu Arg Thr Gln Glu
1156            1160                1165                1170

Val Thr Ser Arg Ile Arg Thr Gln Ser Phe Ser Leu Gln Glu Arg
1171            1175                1180                1185

His Leu Arg Gly Ala Val Pro Trp Ala Phe Asp Pro Pro Gly Pro
1186            1190                1195                1200

Asp Thr Pro Gly Pro
1201            1205
```

Polyclonal antibodies to NO synthase may be obtained using the whole molecule of human NO synthase of the following sequence:

```
                                        SEQ ID NO: 16
Met Gly Asn Leu Lys Ser Val Ala Gln Glu Pro Gly Pro Pro Cys
1               5                   10                  15

Gly Leu Gly Leu Gly Leu Gly Leu Cys Gly Lys Gln Gly
16              20                  25                  30

Pro Ala Thr Pro Ala Pro Glu Pro Ser Arg Ala Pro Ala Ser Leu
31              35                  40                  45

Leu Pro Pro Ala Pro Glu His Ser Pro Ser Ser Pro Leu Thr
46              50                  55                  60

Gln Pro Pro Glu Gly Pro Lys Phe Pro Arg Val Lys Asn Trp Glu
61              65                  70                  75

Val GLys er Ile Thr Tyr Asp Thr Leu Ser Ala Gln Ala Gln Gln
76              80                  85                  90
```

-continued

```
Asp Gly Pro Cys Thr Pro Arg Arg Cys Leu GLys er Leu Val Phe
 91              95                 100                105

Pro Arg Lys Leu Gln Gly Arg Pro Ser Pro Gly Pro Pro Ala Pro
106             110                 115                120

Glu Gln Leu Leu Ser Gln Ala Arg Asp Phe Ile Asn Gln Tyr Tyr
121             125                 130                135

Ser Ser Ile Lys Arg Ser GLys er Gln Ala His Glu Gln Arg Leu
136             140                 145                150

Gln Glu Val Glu Ala Glu Val Ala Ala Thr Gly Thr Tyr Gln Leu
151             155                 160                165

Arg Glu Ser Glu Leu Val Phe Gly Ala Lys Gln Ala Trp Arg Asn
166             170                 175                180

Ala Pro Arg Cys Val Gly Arg Ile Gln Trp Gly Lys Leu Gln Val
181             185                 190                195

Phe Asp Ala Arg Asp Cys Arg Ser Ala Gln Glu Met Phe Thr Tyr
196             200                 205                210

Ile Cys Asn His Ile Lys Tyr Ala Thr Asn Arg Gly Asn Leu Arg
211             215                 220                225

Ser Ala Ile Thr Val Phe Pro Gln Arg Cys Pro Gly Arg Gly Asp
226             230                 235                240

Phe Arg Ile Trp Asn Ser Gln Leu Val Arg Tyr Ala Gly Tyr Arg
241             245                 250                255

Gln Gln Asp GLy Ser Val Arg Gly Asp Pro Ala Asn Val Glu Ile
256             260                 265                270

Thr Glu Leu Cys Ile Gln His Gly Trp Thr Pro Gly Asn Gly Arg
271             275                 280                285

Phe Asp Val Leu Pro Leu Leu Leu Gln Ala Pro Asp Glu Pro Pro
286             290                 295                300

Glu Leu Phe Leu Leu Pro Pro Glu Leu Val Leu Glu Val Pro Leu
301             305                 310                315

Glu His Pro Thr Leu Glu Trp Phe Ala Ala Leu Gly Leu Arg Trp
316             320                 325                330

Tyr Ala Leu Pro Ala Val Ser Asn Met Leu Leu Glu Ile Gly Gly
331             335                 340                345

Leu Glu Phe Pro Ala Ala Pro Phe Ser Gly Trp Tyr Met Ser Thr
346             350                 355                360

Glu Ile Gly Thr Arg Asn Leu Cys Asp Pro His Arg Tyr Asn Ile
361             365                 370                375

Leu Glu Asp Val Ala Val Cys Met Asp Leu Asp Thr Arg Thr Thr
376             380                 385                390

Ser Ser Leu Trp Lys Asp Lys Ala Ala Val Glu Ile Asn Val Ala
391             395                 400                405

Val Leu His Ser Tyr Gln Leu Ala Lys Val Thr Ile Val Asp His
406             410                 415                420

His Ala Thr Ala Ser Phe Met Lys His Leu Glu Asn Glu Gln
421             425                 430                435

Lys Ala Arg Gly Gly Cys Pro Ala Asp Trp Ala Trp Ile Val Pro
436             440                 445                450

Pro Ile Ser GLys er Leu Thr Pro Val Phe His Gln Glu Met Val
451             455                 460                465

Asn Tyr Phe Leu Ser Pro Ala Phe Arg Tyr Gln Pro Asp Pro Trp
466             470                 475                480

Lys Gly Ser Ala Ala Lys Gly Thr Gly Ile Thr Arg Lys Lys Thr
481             485                 490                495
```

```
Phe Lys Glu Val Ala Asn Ala Val Lys Ile Ser Ala Ser Leu Met
496                 500                 505                 510

Gly Thr Val Met Ala Lys Arg Val Lys Ala Thr Ile Leu Tyr Gly
511                 515                 510                 525

Ser Glu Thr Gly Arg Ala Gln Ser Tyr Ala Gln Gln Leu Gly Arg
526                 530                 535                 540

Leu Phe Arg Lys Ala Phe Asp Pro Arg Val Leu Cys Met Asp Glu
541                 545                 550                 555

Tyr Asp Val Val Ser Leu Glu His Glu Thr Leu Val Leu Val Val
556                 560                 565                 570

Thr Ser Thr Phe Gly Asn Gly Asp Pro Glu Asn Gly Glu Ser
571                 575                 580                 585

Phe Ala Ala Ala Leu Met Glu Met Ser Gly Pro Tyr Asn Ser Ser
586                 590                 595                 600

Pro Arg Pro Glu Gln His Lys Ser Tyr Lys Ile Arg Phe Asn Ser
601                 605                 610                 615

Ile Ser Cys Ser Asp Pro Leu Val Ser Ser Trp Arg Arg Lys Arg
616                 620                 625                 630

Lys Glu Ser Ser Asn Thr Asp Ser Ala Gly Ala Leu Gly Thr Leu
631                 635                 640                 645

Arg Phe Cys Val Phe Gly Leu GLys er Arg Ala Tyr Pro His Phe
646                 650                 655                 660

Cys Ala Phe Ala Arg Ala Val Asp Thr Arg Leu Glu Glu Leu Gly
661                 665                 670                 675

Gly Glu Arg Leu Leu Gln Leu Gly Gln Gly Asp Glu Leu Cys Gly
676                 680                 685                 690

Gln Glu Glu Ala Phe Arg Gly Trp Ala Gln Ala Ala Phe Gln Ala
691                 695                 700                 705

Ala Cys Glu Thr Phe Cys Val Gly Glu Asp Ala Lys Ala Ala Ala
706                 710                 715                 720

Arg Asp Ile Phe Ser Pro Lys Arg Ser Trp Lys Arg Gln Arg Tyr
721                 725                 730                 735

Arg Leu Ser Ala Gln Ala Glu Gly Leu Gln Leu Leu Pro Gly Leu
736                 740                 745                 750

Ile His Val His Arg Arg Lys Met Phe Gln Ala Thr Ile Arg Ser
751                 755                 760                 765

Val Glu Asn Leu Gln Ser Ser Lys Ser Thr Arg Ala Thr Ile Leu
766                 770                 775                 780

Val Arg Leu Asp Thr Gly Gly Gln Glu Gly Leu Gln Tyr Gln Pro
781                 785                 790                 795

Gly Asp His Ile Gly Val Cys Pro Pro Asn Arg Pro Gly Leu Val
796                 800                 805                 810

Glu Ala Leu Leu Ser Arg Val Glu Asp Pro Pro Ala Pro Thr Glu
811                 815                 820                 825

Pro Val Ala Val Glu Gln Leu Glu Lys Gly Ser Pro Gly Gly Pro
826                 830                 835                 840

Pro Pro Gly Trp Val Arg Asp Pro Arg Leu Pro Pro Cys Thr Leu
841                 845                 850                 855

Arg Gln Ala Leu Thr Phe Phe Leu Asp Ile Thr Ser Pro Pro Ser
856                 860                 865                 870

Pro Gln Leu Leu Arg Leu Leu Ser Thr Leu Ala Glu Glu Pro Arg
871                 875                 880                 885

Glu Gln Gln Glu Leu Glu Ala Leu Ser Gln Asp Pro Arg Arg Tyr
886                 890                 895                 900
```

-continued

```
Glu Glu Trp Lys Trp Phe Arg Cys Pro Thr Leu Leu Glu Val Leu
901             905                 910                 915

Glu Gln Phe Pro Ser Val Ala Leu Pro Ala Pro Leu Leu Leu Thr
916             920                 925                 930

Gln Leu Pro Leu Leu Gln Pro Arg Tyr Tyr Ser Val Ser Ser Ala
931             935                 940                 945

Pro Ser Thr His Pro Gly Glu Ile His Leu Thr Val Ala Val Leu
946             950                 955                 960

Ala Tyr Arg Thr Gln Asp Gly Leu Gly Pro Leu His Tyr Gly Val
961             965                 970                 975

Cys Ser Thr Trp Leu Ser Gln Leu Lys Pro Gly Asp Pro Val Pro
976             980                 985                 990

Cys Phe Ile Arg Gly Ala Pro Ser Phe Arg Leu Pro Pro Asp Pro
991             995                 1000                1005

Ser Leu Pro Cys Ile Leu Val Gly Pro Gly Thr Gly Ile Ala Pro
1006            1010                1015                1020

Phe Arg Gly Phe Trp Gln Glu Arg Leu His Asp Ile Glu Ser Lys
1021            1025                1030                1035

Gly Leu Gln Pro Thr Pro Met Thr Leu Val Phe Gly Cys Arg Cys
1036            1040                1045                1050

Ser Gln Leu Asp His Leu Tyr Arg Asp Glu Val Gln Asn Ala Gln
1051            1055                1060                1065

Gln Arg Gly Val Phe Gly Arg Val Leu Thr Ala Phe Ser Arg Glu
1066            1070                1075                1080

Pro Asp Asn Pro Lys Thr Tyr Val Gln Asp Ile Leu Arg Thr Glu
1081            1085                1090                1095

Leu Ala Ala Glu Val His Arg Val Leu Cys Leu Glu Arg Gly His
1096            1100                1105                1110

Met Phe Val Cys Gly Asp Val Thr Met Ala Thr Asn Val Leu Gln
1111            1115                1120                1125

Thr Val Gln Arg Ile Leu Ala Thr Glu Gly Asp Met Glu Leu Asp
1126            1130                1135                1140

Glu Ala Gly Asp Val Ile Gly Val Leu Arg Asp Gln Gln Arg Tyr
1141            1145                1150                1155

His Glu Asp Ile Phe Gly Leu Thr Leu Arg Thr Gln Glu Val Thr
1156            1160                1165                1170

Ser Arg Ile Arg Thr Gln Ser Phe Ser Leu Gln Glu Arg Gln Leu
1171            1175                1180                1185

Arg Gly Ala Val Pro Trp Ala Phe Asp Pro Pro Gly Ser Asp Thr
1186            1190                1195                1200

Asn Ser Pro
1201    1203
```

The following sequences of the endothelial NO-synthase fragment is specifically contemplated as suitable antigens:

SEQ ID NO: 17
Pro Trp Ala Phe
1192      1195

SEQ ID NO: 18
Gly Ala Val Pro
1189      1192

SEQ ID NO: 19
                                           Arg
                                          1185
His Leu Arg Gly Ala Val Pro Trp Ala Phe Asp Pro Pro Gly Pro
1186        1190            1195                     1200
Asp Thr Pro Gly Pro
1201        1205

SEQ ID NO: 20
               Ala Phe Asp Pro Pro Gly Pro
               1194 1195               1200
Asp Thr Pro Gly Pro
1201        1205

SEQ ID NO: 21
His Leu Arg Gly Ala Val Pro Trp Ala Phe Asp
1186        1190            1195 1196

SEQ ID NO: 22
His Leu Arg Gly Ala Val Pro Trp Ala Phe Asp Pro Pro Gly Pro
1186        1190            1195                     1200
Asp Thr Pro Gly Pro
1201        1205

The activated potentiated form of each component of the combination may be prepared from initial solution by homeopathic potentization, preferably using the method of proportional concentration decrease by serial dilution of 1 part of each preceding solution (beginning with the initial solution) in 9 parts (for decimal dilution), or in 99 parts (for centesimal dilution), or in 999 parts (for millesimal dilution) of a neutral solvent, coupled with external impact. Preferably, the external impact involves multiple vertical shaking (dynamization) of each dilution. Preferably, separate containers are used for each subsequent dilution up to the required potency level, or the dilution factor. This method is well-accepted in the homeopathic art. See, e.g. V. Schwabe "*Homeopathic medicines*", M., 1967, p. 14-29, incorporated herein by reference for the purpose stated.

For example, to prepare a 12-centesimal dilution (denoted C12), one part of the initial matrix solution of antibodies to C-terminal fragment of beta subunit of human insulin receptor with the concentration of 3.0 mg/ml is diluted in 99 parts of neutral aqueous or aqueous-alcohol solvent (preferably, 15%-ethyl alcohol) and then vertically shaken many times (10 and more) to create the 1st centesimal dilution (denoted as C1). The 2nd centesimal dilution (C2) is prepared from the 1st centesimal dilution C1. This procedure is repeated 11 times to prepare the 12th centesimal dilution C12. Thus, the 12th centesimal dilution C12 represents a solution obtained by 12 serial dilutions of one part of the initial matrix solution of antibodies to C-terminal fragment of beta subunit of human insulin-receptor with the concentration of 3.0 mg/ml in 99 parts of a neutral solvent in different containers, which is equivalent to the centesimal homeopathic dilution C12. Similar procedures with the relevant dilution factor are performed to obtain dilutions C30 and C 200. The intermediate dilutions may be tested in a desired biological model to check activity. The preferred activated potentiated forms for both antibodies comprising the combination of the invention are a mixture of C12, C30, and C200 dilutions. When using the mixture of various homeopathic dilutions (primarily centesimal) of the active substance as biologically active liquid component, each component of the composition (e.g., C12, C30, C200) is prepared separately according to the above-described procedure until the next-to-last dilution is obtained (e.g., until C11, C29, and C199 respectively), and then one part of each component is added in one container according to the mixture composition and mixed with the required quantity of the solvent (e.g. with 97 parts for centesimal dilution).

It is possible to use the active substance as mixture of various homeopathic dilutions, e.g. decimal and/or centesimal (D 20, C 30, C100 or C12, C30, C50 etc.), the efficiency of which is determined experimentally by testing the dilution in a suitable biological model, for example, in models described in the examples herein.

In course of potentiation and concentration decrease, the vertical shaking may be substituted for external exposure to ultrasound, electromagnetic field or any similar external impact procedure accepted in the homeopathic art.

Preferably, the pharmaceutical composition of the invention may be in the form of a liquid or in the solid unit dosage form. The preferred liquid form of the pharmaceutical composition is a mixture, preferably, at a 1:1 ratio of the activated potentiated form of antibodies to C-terminal fragment of beta subunit of human insulin-receptor and the activated potentiated form of antibodies to endothelial NO-synthase. The preferred liquid carrier is water or water-ethyl alcohol mixture.

The solid unit dosage form of the pharmaceutical composition of the invention may be prepared by using impregnating a solid, pharmaceutically acceptable carrier with the mixture of the activated potentiated form aqueous or aqueous-alcohol solutions of active components are mixed, primarily in 1:1 ratio and used in liquid dosage form. Alternatively, the carrier may be impregnated consecutively with each requisite dilution. Both orders of impregnation are acceptable.

Preferably, the pharmaceutical composition in the solid unit dosage form is prepared from granules of the pharmaceutically acceptable carrier which was previously saturated with the aqueous or aqueous-alcoholic dilutions of the activated potentiated form of antibodies to C-terminal fragment of beta subunit of human insulin-receptor and the activated potentiated form of antibodies to endothelial NO-synthase. The solid dosage form may be in any form known in the pharmaceutical art, including a tablet, a capsule, a lozenge, and others. As an inactive pharmaceutical ingredients one can use glucose, sucrose, maltose, amylum, isomaltose, isomalt and other mono- olygo- and polysaccharides used in manufacturing of pharmaceuticals as well as technological mixtures of the above mentioned inactive pharmaceutical ingredients with other pharmaceutically acceptable excipients, for example isomalt, crospovidone, sodium cyclamate, sodium saccharine, anhydrous citric acid etc), including lubricants, disintegrants, binders and coloring agents. The preferred carriers are lactose and isomalt. The pharmaceutical dosage form may further include standard pharmaceutical excipients, for example, microcrystalline cellulose and magnesium stearate.

To prepare the solid oral form, 100-300 μm granules of lactose are impregnated with aqueous or aqueous-alcoholic solutions of the activated potentiated form of antibodies to histamine, activated-potentiated form of antibodies to C-terminal fragment of beta subunit of human insulin-receptor and the activated potentiated form of antibodies to endothelial NO-synthase in the ratio of 1 kg of antibody solution to 5 or 10 kg of lactose (1:5 to 1:10). To effect impregnation, the lactose granules are exposed to saturation irrigation in the fluidized boiling bed in a boiling bed plant (e.g. "Hüttlin Pilotlab" by Hüttlin GmbH) with subsequent drying via heated air flow at a temperature below 40° C. The estimated quantity of the dried granules (10 to 34 weight parts) saturated with the activated potentiated form of antibodies is placed in the mixer, and mixed with 25 to 45 weight parts of "non-saturated" pure lactose (used for the purposes of cost reduction and simplification and acceleration of the technological process without decreasing the treatment efficiency), together with 0.1 to 1 weight parts of magnesium stearate, and 3 to 10 weight parts of microcrystalline cellulose. The obtained tablet mass is uniformly mixed, and tableted by direct dry pressing (e.g., in a Korsch—XL 400 tablet press) to form 150 to 500 mg round pills, preferably, 300 mg. After tableting, 300 mg pills are obtained that are saturated with aqueous-alcohol solution (3.0-6.0 mg/pill) of the combination of the activated potentiated form of antibodies to C-terminal fragment of beta subunit of human insulin-receptor and the activated potentiated form of antibodies to endothelial NO-synthase. Each component of the combination used to impregnate the carrier is in the form of a mixture of centesimal homeopathic dilutions C12, C30, and C50 or a mixture of centesimal homeopathic dilutions C12, C30 and C200.

While the invention is not limited to any specific theory, it is believed that the activated potentiated form of the antibodies described herein do not contain the molecular form of the antibody in the amount sufficient to have biological activity attributed to such molecular form. The biological activity of the combination of the invention is amply demonstrated in the appended examples.

The pharmaceutical composition of the invention may be used for administration to patients having any type of diabetes.

The said pharmaceutical composition can be used in the treatment of Diabetes Mellitus as a monotherapy of hyperglycaemia and in the complex therapy as an add-on to insulin replacement therapy; and/or with oral hypoglycemic agents such as biguanides (metformin); sulfonylureas (glybenclamide, glipizide, gliclazide, glicvidone, glimepiride); thiazolidinediones (rosiglitazone); alpha-glucosidase inhibitors (acarbose) etc; as well as add-on to accompanying therapy of Diabetes Mellitus to prevent diabetic complications.

As shown in the appended examples, the administration of the combination of the invention to such patients improves blood glucose levels.

EXAMPLES

Example 1

The two experimental studies investigated the effects of antibodies to the C-terminal fragment to the insulin receptor (β-subunit affinity purified on antigen, in ultra-low dose, obtained by super dilution of the initial matrix solution $100^{12}$, $100^{30}$, $100^{200}$ times (ULD anti-IR), antibodies to endothelial NO-synthase affinity purified on antigen, in ultra-low dose, obtained by hyper-dilution of the initial matrix solution $100^{12}$, $100^{30}$, $100^{200}$ (ULD anti-ULD anti-eNOS), as well as the combination of ultra-low doses of antibodies to the C-terminal fragment to the insulin receptor β-subunit and ultra-low dose of antibodies to endothelial NO-synthase (ULD anti-IR+ULD anti-eNOS).

According to World Health Organization (WHO) criteria, diabetes mellitus (types I and II) is characterized by an increase in the blood glucose level (hyperglycemia) and by glucose tolerance disturbance. The latter can be caused by abnormal insulin secretion and/or by decreased insulin sensitivity of peripheral tissues. The glucose-tolerance test, based on dynamic evaluation of the ability of body tissues to utilize glucose, is a sensitive method of evaluating disturbance of body issue glucose tolerance.

Study 1.

In the study, 150 male Wistar were used (weight at beginning of study 250-300 g, age 3.5-4 months). 10 rats were intact. The rest were intravenously injected with streptozotocin at the dose of 50 mg/kg (experimental model of diabetes mellitus). 72 hours after injection of streptozotocin, rats with blood plasma glucose level not less than 12 mmol/l were selected, divided into 7 groups (20 rats in each), which over 21 days were given distilled water (5 ml/kg/day, once daily intragastrically), insulin (8 units/kg/day, subcutaneously), Rosiglitazone (8 mg/kg/day, twice daily intragastrically), ULD anti-IR (2.5 ml/kg/day in a volume of 5 ml/kg/day, once daily intragastrically), ULD anti-IR+ULD anti-eNOS (5 ml/kg/day, once daily intragastrically), and also Rosiglitazone and insulin together or ULD anti-IR+ULD anti-eNOS and insulin, according to regimes corresponding to each preparation (as described above). Intact rats received distilled water in the same volume. On days 7, 14 and 21 of injection of preparations in rats, fasting blood plasma glucose level measured with enzymatic method (glucose oxidase method) with utilization of "glucose FKD" kits (Russia).

Oral glucose tolerance test (OGTT) was performed on day 14 of the study (day 14 of administration of preparation) according to standard method (Du Vigneaud and Karr, 1925). The rats were starving at water for 18 hours. 60 min before the test they were last given test substances. Intact rats received distilled water in the same volume. Glucose was administered per os 50% w/w water glucose solution (1 g/kg of rat weight). Serum glucose of blood sample from tail vein was measured by using "Glucose FKD" kit (OOO "Pharamaceutical and clinical diagnostics, Russia) at 0, 30, 60, 90, 120 min. Mean area under the curve (AUC) concentration of blood glucose over time was calculated.

Injection of streptozotocin led to a substantial increase in blood plasma glucose of rats in comparison with intact animals (18 mmol/l versus 3.5 mmol/l, $p<0.05$). In the ULD anti-IR group, on day 7, 14 and 21 of injection of preparation, glucose level was lower than in the control group by 22-28% on average; however, differences did not reach a statistically significant level. The combination of ULD anti-IR and anti-eNOS was more efficacious; the decrease in glucose level on days 14 and 21 of the experiment were 47% and 42%, respectively ($p<0.05$ versus control). The reference preparation, Rosiglitazone, also lowered glucose level by day 14 and 21 of the experiment; at that, the effect reached statistical significance on day 14 of the experiment only (36%, $p<0.05$ versus control).

Insulin, injected at ½ of the effective dose (selected in the preliminary study) most effectively lowered glucose level in all observation periods (down to the level of the intact control). (FIG. 1). It should be taken into account that short-acting insulin was used in the study and blood plasma glucose was measured 1 hour after its injection, which also influenced the effect of the ½ insulin dose on blood glucose level. Against this background it was not possible to fully determine what the effect of the combined use of insulin and rosiglitazone or insulin and complex ULD anti-IR+anti-eNOS is.

Figure 2:
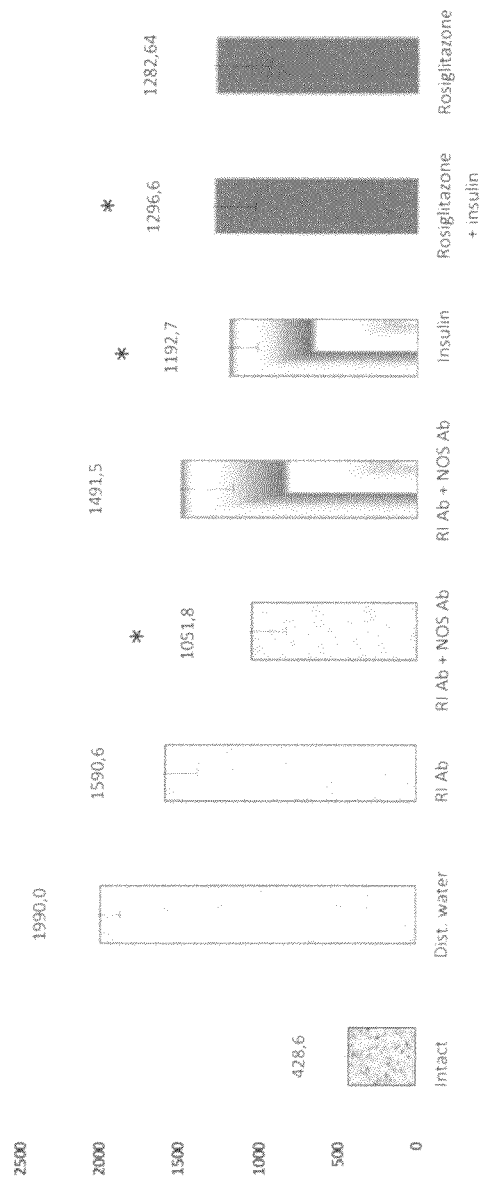

Glucose tolerance disturbance (reduction in glucose utilization by the body) is one of the most important indicators in diagnostic and treatment of diabetes mellitus. In intact animals, in the oral glucose tolerance test (day 14 of injection of preparations), complex preparation ULD anti-IR+ULD anti-eNOS and insulin most effectively increased glucose tolerance when administered alone. Rosiglitazone also reduced the area under concentration over time curve (increased glucose tolerance); however, its efficacy was not statistically significant versus the control group (FIG. 2).

Study 2.

In the study, 36 male Goto-Kakizaki rats were used (weight at beginning of study 250-280 g, age 10-12 weeks). Rats of this line are characterized by spontaneous development of non-insulin-dependent diabetes. The animals were divided into 3 groups (12 rats in each) and received either distilled water (5 ml/kg, once daily intragastrically), or ULD anti-IR (2.5 ml/kg once daily intragastrically), or ULD anti-IR+ULD anti-eNOS (5 ml/kg, once daily intragastrically) for 28 days. Blood plasma glucose level was measured with the help of a glucose analyzer (Beckman, Fullerton, Calif., USA) before beginning injection of preparations and on day 4, 8, 12, 16, 20, 24, 28 of injection of preparations. On day 28, a glucose tolerance test was carried out (glucose p.o., 1 g/kg).

Figure 3:
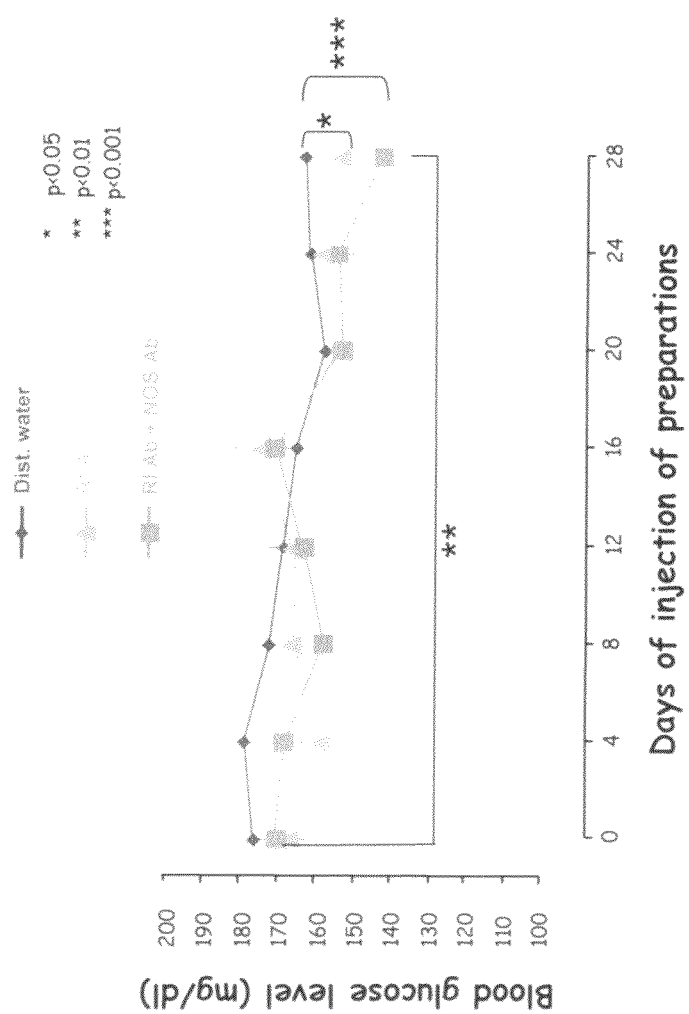
FIG. 3—Illustrates the effect of tested preparations on blood plasma glucose level of rats with spontaneous non-insulin-dependent diabetes mellitus.

Injection of ULD anti-IR led to a significant ($p<0.05$) drop in blood plasma glucose level of rats; however, the use of complex ULD anti-IR+ULD anti-eNOS was more efficacious ($p<0.001$ versus control) (FIG. 3).

Figure 4:
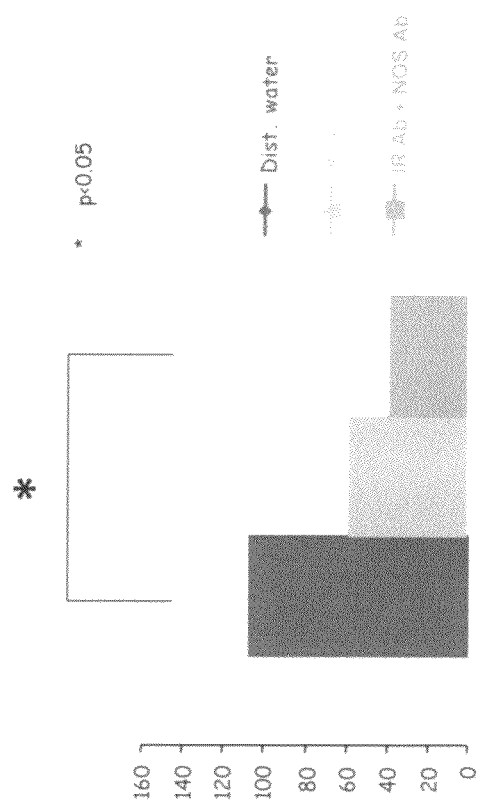
FIG. 4—Illustrates the effect of tested preparations on day 28 of injection on indicators of area under concentration-time curve (AUC) in glucose tolerance test in rats with spontaneous non-insulin-dependent diabetes mellitus.

The results were confirmed by glucose tolerance test data carried out on day 28 of injection of preparations (FIG. 4). Injection of ULD anti-IR led to an increase in glucose tolerance (statistically insignificant drop by 44% AUC versus control). At the same time, the reduction in this parameter (AUC) caused by injection of complex ULD anti-IR+ULD anti-eNOS was 62% and it was statistically significant versus control ($p<0.05$).

Example 2

A clinical study of combination of ultra-low doses of antibodies to the beta subunit C-terminal fragment of the insulin receptor (ULD anti-IR) and ultra-low doses of antibodies to endothelial NO-synthase (ULD anti-eNOS), each in the form of water-alcohol mixture of homeopathic dilutions C12, C30, and C200 impregnated onto isomalt was carried in humans.

An open-label noncomparative study of the efficacy and safety of ULD anti-IR+ULD anti-eNOS in patients with type 1 diabetes mellitus (DM) included patients with a diagnosis of DM type 1 of mild to moderate severity without signs of serious macro- and microvascular pathology. After obtaining the patient's voluntary informed consent for participation in the clinical trial, an initial survey was conducted for the purpose of establishing whether the patient met inclusion/exclusion criteria. A 2-week "wash-out period" was provided before the beginning of the study, during which an examination of patients was carried out (complaints, fasting glycemia, glycated hemoglobin, daily glycemic profile and lipoproteinogram as well and efficacy and safety of current treatment were assessed). In a 12-week study, the key endpoints were measured in the "wash-out" weeks, then at weeks 6 and 12 of the treatment. In 4 patients, during the "wash-out" period and at the end of the study, continuous monitoring of glycemic level had been carried out with the help of the CGMS system. The continuous glucose monitoring system (CGMS) makes it possible to control the glucose level over three days. The test results show how glucose level changes over 3 days, depending on insulin therapy and life style. This data helps to distinguish periods of high or low glucose level depending on diet, medications intake or physical load. The system in graphic form shows minimum glucose level of 2.2 mmol/L, maximum values up to 22.2 mmol/L, and also mean daily blood glucose level.

Patients with DM type 1, mild to moderate severity, at the decompensation stage, received standard insulin therapy before inclusion and during the study:

1. Long-acting insulins (PROTAPHANE®, LANTUS®) in average doses from 12 to 26 U/day.
2. Short-acting insulins (APIDRA®, NOVORAPID®, Aktropid) in the average doses:
   morning 8-10 U/day
   lunch 8-12 U/day
   supper 8-13 U/day.

After confirming the patient's ability to participate, the patient was included in the study and, as an add-onn to standard therapy of DM type 1 received the ULD anti-IR+ULD anti-eNOS preparation; the administration regimen depended on the degree of severity and compensation of the DM type 1. Patients included in the study received therapy by ULD anti-IR+ULD anti-eNOS preparation in different dosages:

1. Four patients—1 tablet 4 times a day at 8:00 AM, 12:00 PM, 6:00 PM, 10:00 PM.
2. Two patients—1 tablet 2 times a day at 8:00 AM, 6:00 PM.

On weeks 3 and 8, the daily glycemic profile was also controlled (eight-point measurement) and patients were contacted by phone (telephone "visits"). Clinical examinations were done every week. As a total, the patients had been observed for 14 weeks.

Six patients were included in the study, five of whom completed according to the study protocol. Evaluation of glycemia was carried out by eight-point daily glucose profile at a baseline and after 3, 6 and 12 weeks of treatment. The level of glycated hemoglobin was determined at a baseline and after 12 weeks of therapy.

All DM type 1 patients included in the study noted that daily glycemia tended to fall after 6-week therapy with the study drugs. According to eight-point daily glucose profile, an average drop in glycemia of 20% was recorded in patients with DM type 1. After 12 weeks of therapy, glycated hemoglobin was on average 10-15% lower in comparison with the baseline value.

According to the results of continuous glucose monitoring with the CGMS system in all patients, 3-month therapy by ULD anti-IR+ULD anti-eNOS resulted in a reduction in mean daily glycemia and decreased oscillations of minimum and maximum glycemia of 15-20% of the baseline.

Figure 5:
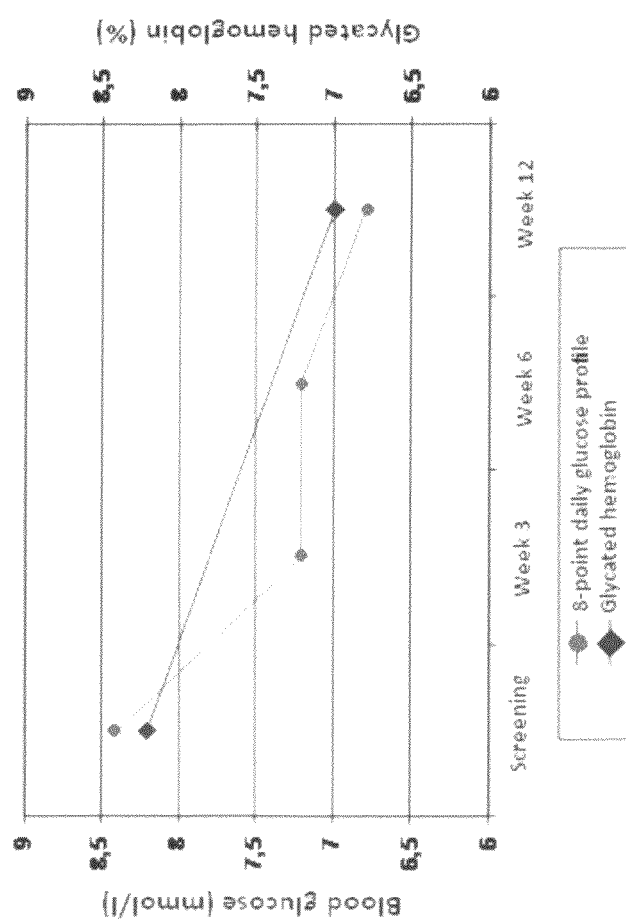
FIG. 5—Illustrates the dynamics of glucose and glycolated hemoglobin levels in patients with type 1 diabetes mellitus against background of taking IR Ab+NOS Ab preparation.

In patient No. 103 with DM type 1 at a decompensation stage, a significant drop in daily glycemia of 48% was unexpectedly observed (1 week—8.0 mmol/L, 12 weeks—4.8 mmol/L), which required a correction of insulin therapy (reduction in daily dose of short-acting insulin down to 8 U/d). The dynamics of the mean blood glucose level and glycated hemoglobin is shown in FIG. 5.

In the course of the study, no adverse events including serious adverse one were recorded, which evidences the safety of the preparation.

Example 3

A clinical study of combination of ultra-low doses of antibodies to the beta subunit C-terminal fragment of the insulin receptor (ULD anti-IR) and ultra-low doses of antibodies to endothelial NO-synthase (ULD anti-eNOS), each in the form of water-alcohol mixture of homeopathic dilutions C12, C30, and C200 impregnated onto isomalt was carried in humans.

An open-label noncomparative study of the efficacy and safety of ULD anti-IR+ULD anti-eNOS in patients with type 2 diabetes mellitus (DM) included patients with a diagnosis of DM type 2 of mild to moderate severity without signs of serious macro- and microvascular pathology, who received average therapeutic doses of Metformin. After obtaining the patient's voluntary informed consent for participation in the clinical trial, an initial survey was conducted for the purpose of establishing whether the patient met inclusion/exclusion criteria. Upon confirmation of the possibility of participating in the study, the patient received 1 tablet of Subbetta 4 times a day in addition to type 2 DM standard therapy. A 2-week "wash-out period" was provided before the beginning of the study, during which an examination of patients was carried out (complaints, fasting glycemia, glycated hemoglobin, daily glycemic profile and lipoproteinogram, insulin resistance index indicators (HOMA-IR) as well and efficacy and safety of current treatment were assessed). In a 12-week study, the key endpoints were measured in the "wash-out" weeks, then at weeks 6 and 12 of the treatment. In 4 patients, during the "wash-out" period and at the end of the study, continuous monitoring of glycemic level had been carried out with the help of the CGMS system. On weeks 3 and 8, eight-point glycemic profile was additionally controlled and telephone "visits" were conducted. Clinical condition was checked every week. On the whole, the patient was observed over 14 weeks.

Eleven patients with type 2 DM type 2 at decompensation stage were included in the study. One patient voluntary dropped out of the study. The remaining patients continue the treatment. In DM type 2 patients, according to eight-point daily profile data, an average drop in glycemia of 20% was registered by the week 6. On week 12, an average drop in glycated hemoglobin of 15-19% of the baseline value was noted.

In all patients in the course of 12 weeks, blood test parameters (erythrocytes, hemoglobin, leukocytes, thrombocytes, leukocyte formula, ESR), lipoproteinogram, EKG, assay of hepatic function (ALT, AST, bilirubin and its fractions) remained within normal limits. Insulin resistance, determined by HOMA-IR test, dropped on average by 17-19% of the baseline value.

In 12-week course of the study, no adverse events including serious adverse one were recorded, which evidences the safety of the preparation. No abnormalities in liver functional activity were also revealed.

Figure 6:
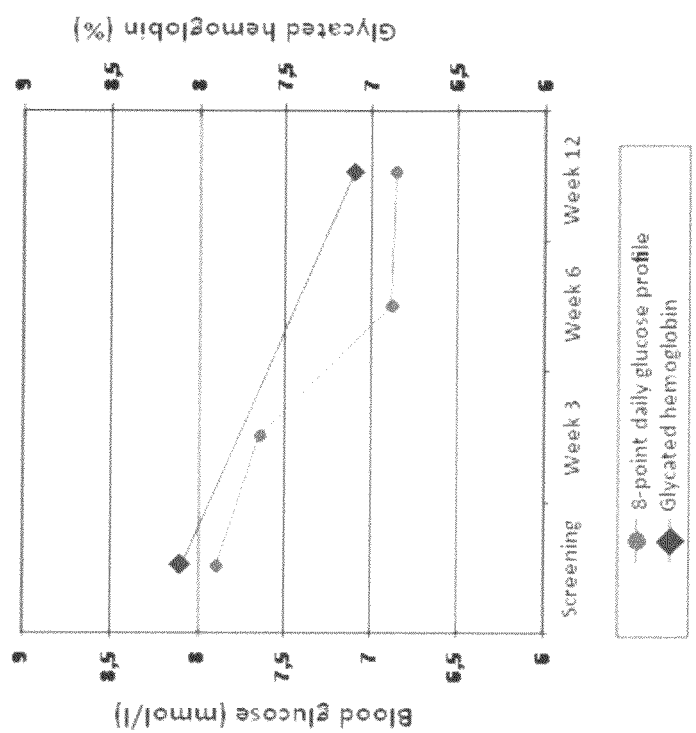
FIG. 6—Illustrates the dynamics of glucose and glycolated hemoglobin levels in patients with type 2 diabetes mellitus against background of taking IR Ab+NOS Ab preparation.

The dynamics of the mean blood glucose level and glycated hemoglobin are shown in FIG. 6.

Example 4

A patient X. (male, 74 years old) diagnosed with Diabetes type II has been receiving Maninil (Glibenclamide, Berlin—Chemie) at a dose of 5 mg twice a day. A deep necrotic foot ulcer at the calcaneal bone was appeared 3 years ago despite the treatment he was given. The patient was twice hospitalized on a surgical ward; however, the treatment did not result in significant improvement. A claimed pharmaceutical composition, a tablet of 250 mg, comprising activated potentiated form (ultra-low doses) of antibodies to C-terminal of insulin receptor beta subunit (Ab RI) and endothelial NO synthase (Ab NOS) impregnated on isomalt as a mixture of water-ethanol homeopathic dilutions C12, C30, C200 (Ab RI+Ab NOS) was added to the Maninil therapy. As a result of one-month treatment the dose of Maninil was reduced to 5 mg daily (one tablet before sleep). Glucose blood level dropped to normal values (from 8-10 mmol/L to 5-6 mmol/L). The given therapy turned back development of the foot ulcer. The ulcer cleared of necrotic masses and cuticularised. On examination the ulcer has gone, there is round white area (3.5 cm in diameter) of peeling skin at the calcaneal bone.

What is claimed is:

1. A pharmaceutical composition comprising a) an activated-potentiated form of an antibody to human insulin receptor, and b) an activated-potentiated form of an antibody to endothelial NO synthase.

2. A pharmaceutical composition comprising a) an activated-potentiated form of an antibody to a C-terminal fragment of the beta subunit of human insulin receptor, and b) an activated-potentiated form of an antibody to endothelial NO-synthase.

3. A pharmaceutical composition comprising a) an activated-potentiated form of an antibody to human insulin receptor, and b) an activated-potentiated form of an antibody to endothelial NO-synthase, wherein the insulin receptor consists of one alpha subunit and one beta subunit.

4. A pharmaceutical composition comprising pharmaceutically acceptable solid carrier, and a) an activated-potentiated form of an antibody to a C-terminal fragment of the beta subunit of human insulin receptor in the form of a mixture of C12, C30, and C200 homeopathic dilutions impregnated onto said solid carrier, and b) activated-potentiated form of an antibody to endothelial NO-synthase in the form of mixture of C12, C30, and C200 homeopathic dilutions impregnated onto said solid carrier.

5. The pharmaceutical composition of claim 1, 2, 3, or 4, wherein said antibody to human insulin receptor is monoclonal, polyclonal or natural antibody.

6. The pharmaceutical composition of claim 5, wherein said antibody to human insulin receptor is a polyclonal antibody.

7. The pharmaceutical composition of claim 6, the activated-potentiated form of an antibody to a human insulin receptor is prepared by successive centesimal dilutions coupled with shaking of every dilution.

8. The pharmaceutical composition of claim 1, 2, 3, or 4, wherein said antibody to endothelial NO-synthase is monoclonal, polyclonal or natural antibody.

9. The pharmaceutical composition of claim 8, wherein said antibody to endothelial NO-synthase is a polyclonal antibody.

10. The pharmaceutical composition of claim 9, the activated-potentiated form of an antibody to endothelial NO-synthase is prepared by successive centesimal dilutions coupled with shaking of every dilution.

11. The pharmaceutical composition of claim 1, wherein said human insulin receptor consists of sequence selected from group consisting of in SEQ ID No: 1, SEQ ID No: 2, SEQ ID No: 3, SEQ ID No: 4, SEQ ID No: 5, SEQ ID No: 6, SEQ ID No: 7, SEQ ID No: 8, SEQ ID No: 9, SEQ ID No: 10, SEQ ID No: 11, SEQ ID No: 12, SEQ ID No: 13, SEQ ID No: 14.

12. The pharmaceutical composition of claim 1, wherein said endothelial NO synthase consists of sequence provided in SEQ. ID No. 15, SEQ ID No: 16, SEQ ID No: 17, SEQ ID No: 18, SEQ ID No: 19, SEQ ID No: 20, SEQ ID No: 21, SEQ ID No: 22.

* * * * *